(12) United States Patent
Nolle

(10) Patent No.: US 10,336,799 B2
(45) Date of Patent: Jul. 2, 2019

(54) FIBROBLAST GROWTH FACTOR MUTEINS WITH INCREASED ACTIVITY

(71) Applicant: Miltenyi Biotec GmbH, Bergisch-Gladbach (DE)

(72) Inventor: Volker Nolle, Kurten (DE)

(73) Assignee: Miltenyi Biotec GmbH, Bergisch, Gladbach (DE)

( * ) Notice: Subject to any disclaimer, the term of this patent is extended or adjusted under 35 U.S.C. 154(b) by 53 days.

(21) Appl. No.: 14/679,872

(22) Filed: Apr. 6, 2015

(65) Prior Publication Data
US 2015/0284443 A1   Oct. 8, 2015

(30) Foreign Application Priority Data

Apr. 7, 2014   (EP) .................................. 14163764

(51) Int. Cl.
C12N 5/00      (2006.01)
C07K 14/50     (2006.01)

(52) U.S. Cl.
CPC .......... C07K 14/503 (2013.01); C12N 5/0018 (2013.01); *C12N 2501/115* (2013.01)

(58) Field of Classification Search
None
See application file for complete search history.

(56) References Cited

U.S. PATENT DOCUMENTS

| | | | | |
|---|---|---|---|---|
| 5,859,208 A * | 1/1999 | Fiddes | ............... | A61K 38/1825 530/350 |
| 6,083,706 A | 7/2000 | Florkiewicz et al. | | |
| 8,772,460 B2 * | 7/2014 | Chen | ............... | C07K 14/503 435/375 |
| 9,169,309 B2 * | 10/2015 | Jeong | ............... | C12N 5/0606 |
| 2010/0298220 A1 * | 11/2010 | Blaber | ............... | A61K 38/18 514/9.1 |
| 2012/0225479 A1 * | 9/2012 | Jeong | ............... | C12N 5/0606 435/351 |
| 2013/0236959 A1 * | 9/2013 | Chen | ............... | C07K 14/503 435/360 |

FOREIGN PATENT DOCUMENTS

| | | |
|---|---|---|
| EP | 1444995 A1 | 11/2004 |
| WO | WO-2003/094835 A2 | 11/2003 |
| WO | WO-2003/094835 A3 | 11/2003 |
| WO | WO-2010/135491 A2 | 11/2010 |
| WO | WO-2013/090919 A1 | 6/2013 |

OTHER PUBLICATIONS

Arakawa, T. et al. (1989). "Characterization of a Cysteine-Free Analong of Recombinant Human Basic Fibroblast Growth Factor", *Biochemical and Biophysical Research Communications*, 161(1):335-341.
Caccia, P. et al. (1992). "Stablization of recombinant human basic fibroblast growth factor by chemical modifications of cysteine residues", *Eur. J. Biochem*, 204:649-655.
Extended European Search Report dated Sep. 22, 2014, for European Patent Application No. 14163764.5, 6 pages.
Fox G.M. et al. (1988). "Production, Biological Activity, and Structure of Recombinant Basic Fibroblast Growth Factor and an Analog with Cysteine Replaced by Serine", *The Journal of Biological Chemistry*, 263(34):18452-18458.
Furue M.K. et al. (2008). "Heparin promotes the growth of human embryonic stem cells in a defined serum-free medium", *Proc Natl Acad Sci USA*, 105(36):13409-13414.
Heath, W.F. et al. (1991). "Mutations in the Heparin-Binding Domains of Human Basic Fibroblast Growth Factor Alter Its Biological Activity", *Biochemistry*, 30:5608-5615.
Levenstein, M.E. et al. (2006). "Basic Fibroblast Growth Factor Support of Human Embryonic Stem Cell Self-Renewal", *Stem Cells*, 24:568-574.
Nguyen, T.H. et al. (2013). "A Heparin-Mimicking Polymer Conjugate Stabilizes Basic Fibroblast Growth Factor (bFGF)", *Nat Chem.*, 5(3):221-227.
Rinas, U. et al. (1992). "Cysteine to Serine Substitution in Basic Fibroblast Growth Factor: Effect on Inclusion Body Formation and Proteolytic Susceptibility During In Vitro Refolding", *Bio/Technology*, 10:435-440.
Robinson, C.J. et al. (1994). "The International Standard for Basic Fibroblast Growth Factor (FGF-2); Comparison of Candidate Preparations by In Vitro Bioassays and Immunoassays", *Growth Factors*, 11:9-16.
Seno, M. et al. (1988). "Stabilizing Basic Fibroblast Growth Factor Using Protein Engineering", *Biochemical and Biophysical Research Communications*, 151(2):701-708.
Shahrokh Z. et al. (1994) "Disulfide-Linked Oligomerization of Basic Fibroblast Growth Factor", Chapter 6 in: *Formulation and Delivery of Proteins and Peptides*, Eds. Cleland J.L. and Langer R., ACS Symposium Series, 567:85-99.

* cited by examiner

*Primary Examiner* — Marianne P Allen
(74) *Attorney, Agent, or Firm* — Morrison & Foerster LLP

(57) ABSTRACT

The present invention provides FGF-2 polypeptides that differ from the wild-type FGF-2 (SEQ ID NO:1) at least at amino acid position 56, 102 and 119, wherein the differences are Q56I, N102G, K119N substitutions, leading to FGF-2 polypeptides with higher thermostability, higher biological activity and higher resistance to proteolytic degradation. These polypeptides can be used in cell culture media.

6 Claims, 11 Drawing Sheets

Specification includes a Sequence Listing.

FIG. 1

```
WT-isoform-1    ---------PALPEDGGSGAFPPGHFKDPKRLYCKNGGFFLRIHPDGRVDGVREKSDPHI    51
WT-isoform-3    MAAGSITTLPALPEDGGSGAFPPGHFKDPKRLYCKNGGFFLRIHPDGRVDGVREKSDPHI    60
                         *************************************************

WT-isoform-1    KLQLQAEERGVVSIKGVCANRYLAMKEDGRLLASKCVTDECFFFERLESNNYNTYRSRKY   111
WT-isoform-3    KLQLQAEERGVVSIKGVCANRYLAMKEDGRLLASKCVTDECFFFERLESNNYNTYRSRKY   120
                ************************************************************

WT-isoform-1    TSWYVALKRTGQYKLGSKTGPGQKAILFLPMSAKS   146
WT-isoform-3    TSWYVALKRTGQYKLGSKTGPGQKAILFLPMSAKS   155
                **********************************
```

FIG. 2

```
5x-mutein_mb   PALPEDGGSGAFPPGHFKDPKRLYCKNGGFFLRIHPDGRVDGVREKSDPHIKLQLIAEER    60
WT-isoform-1   PALPEDGGSGAFPPGHFKDPKRLYCKNGGFFLRIHPDGRVDGVREKSDPHIKLQLIAEER    60
4x-mutein_mb   PALPEDGGSGAFPPGHFKDPKRLYCKNGGFFLRIHPDGRVDGVREKSDPHIKLQLIAEER    60
2x-mutein_mb   PALPEDGGSGAFPPGHFKDPKRLYCKNGGFFLRIHPDGRVDGVREKSDPHIKLQLIAEER    60
3x-mutein_mb   PALPEDGGSGAFPPGHFKDPKRLYCKNGGFFLRIHPDGRVDGVREKSDPHIKLQLQAEER    60
               ************************************************** *******

5x-mutein_mb   GVVSIKGVSANRYLAMKEDGRLLASKSVTDECFFFERLESNGYNTYRSRKYTSWYVALNR   120
WT-isoform-1   GVVSIRGVSIRGVCANRYLAMKEDGRLLASKCVTDECFFFERLESNGYNTYRSRKYTSWYVALKR   120
4x-mutein_mb   GVVSIKGVCANRYLCMKEDGRLLASKCVTDECFFFERLESNNYNTYRSRKYTSWYVALNR   120
2x-mutein_mb   GVVSIKGVCANRYLAMKEDGRLLASKCVTDECFFFERLESNGYNTYRSRKYTSWYVALKR   120
3x-mutein_mb   GVVSIKGVCANRYLAMKEDGRLLASKCVTDECFFFERLESNGYNTYRSRKYTSWYVALNR   120
               ******.****. ****.************:***********  ***************

5x-mutein_mb   TGQYKLGSKTGPGQKAILFLPMSAKS   146
WT-isoform-1   TGQYKLGSKTGPGQKAILFLPMSAKS   146
4x-mutein_mb   TGQYKLGSKTGPGQKAILFLPMSAKS   146
2x-mutein_mb   TGQYKLGSKTGPGQKAILFLPMSAKS   146
3x-mutein_mb   TGQYKLGSKTGPGQKAILFLPMSAKS   146
               **************************
```

SEQUENCE LISTING

<160> NUMBER OF SEQ ID NOS: 6

<210> SEQ ID NO 1
<211> LENGTH: 146
<212> TYPE: PRT
<213> ORGANISM: Homo sapiens

<400> SEQUENCE: 1

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 2
<211> LENGTH: 155
<212> TYPE: PRT
<213> ORGANISM: Homo sapiens

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 3
<211> LENGTH: 146
<212> TYPE: PRT
<213> ORGANISM: Artificial Sequence
<220> FEATURE:
<223> OTHER INFORMATION: Synthetic Construct

<400> SEQUENCE: 3

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
            35                  40                  45

Pro His Ile Lys Leu Gln Leu Ile Ala Glu Glu Arg Gly Val Val Ser
        50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Gly Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
            130                 135                 140

Lys Ser
145

<210> SEQ ID NO 4
<211> LENGTH: 146
<212> TYPE: PRT
<213> ORGANISM: Artificial Sequence
<220> FEATURE:
<223> OTHER INFORMATION: Synthetic Construct

<400> SEQUENCE: 4

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu

```
            20                  25                  30
Arg Ile His Pro Asp Gly Arg Val Asp Gly Val Arg Glu Lys Ser Asp
            35                  40                  45

Pro His Ile Lys Leu Gln Leu Ile Ala Glu Glu Arg Gly Val Val Ser
        50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Gly Tyr Asn Thr Tyr Arg Ser Arg Lys Tyr Thr
            100                 105                 110

Ser Trp Tyr Val Ala Leu Asn Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 5
<211> LENGTH: 146
<212> TYPE: PRT
<213> ORGANISM: Artificial Sequence
<220> FEATURE:
<223> OTHER INFORMATION: Synthetic Construct

<400> SEQUENCE: 5

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
            35                  40                  45

Pro His Ile Lys Leu Gln Leu Ile Ala Glu Glu Arg Gly Val Val Ser
        50                  55                  60

Ile Lys Gly Val Cys Ala Asn Arg Tyr Leu Cys Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Gly Tyr Asn Thr Tyr Arg Ser Arg Lys Tyr Thr
            100                 105                 110

Ser Trp Tyr Val Ala Leu Asn Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 6
<211> LENGTH: 146
<212> TYPE: PRT
<213> ORGANISM: Artificial Sequence
<220> FEATURE:
<223> OTHER INFORMATION: Synthetic Construct

<400> SEQUENCE: 6

Pro Ala Leu Pro Glu Asp Gly Gly Ser Gly Ala Phe Pro Pro Gly His
1               5                   10                  15
```

```
Phe Lys Asp Pro Lys Arg Leu Tyr Cys Lys Asn Gly Gly Phe Phe Leu
            20              25              30

Arg Ile His Pro Asp Gly Arg Val Asp Gly Val Arg Glu Lys Ser Asp
        35              40              45

Pro His Ile Lys Leu Gln Leu Ile Ala Glu Glu Arg Gly Val Val Ser
    50              55              60

Ile Lys Gly Val Ser Ala Asn Arg Tyr Leu Ala Met Lys Glu Asp Gly
65              70              75              80

Arg Leu Leu Ala Ser Lys Ser Val Thr Asp Glu Cys Phe Phe Phe Glu
            85              90              95

Arg Leu Glu Ser Asn Gly Tyr Asn Thr Tyr Arg Ser Arg Lys Tyr Thr
            100             105             110

Ser Trp Tyr Val Ala Leu Asn Arg Thr Gly Gln Tyr Lys Leu Gly Ser
        115             120             125

Lys Thr Gly Pro Gly Gln Lys Ala Ile Leu Phe Leu Pro Met Ser Ala
        130             135             140

Lys Ser
145
```

US 10,336,799 B2

FIBROBLAST GROWTH FACTOR MUTEINS WITH INCREASED ACTIVITY

CROSS REFERENCE TO RELATED APPLICATIONS

This application claims priority to European Application No. EP14163764.5, filed Apr. 7, 2014, incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 212302002800SEQLIST.txt, date recorded: Apr. 3, 2015, size: 8 KB).

FIELD OF THE INVENTION

The invention relates generally to muteins of fibroblast growth factor-two (FGF-2) polypeptides which have a higher thermostability, a higher biological activity and a higher resistance to proteolytic degradation than wild-type FGF-2.

BACKGROUND OF THE INVENTION

Fibroblast growth factor-2 (FGF-2), also called basic fibroblast growth factor (bFGF), is a cytokine which plays a role in the regulation of cell survival, cell division, angiogenesis, cell differentiation and cell migration. It functions as potent mitogen in vitro and is used for the stimulation and proliferation of a wide variety of cell types including human pluripotent cells, mesenchymal stem cells, bone marrow stromal cells and neural stem cells. FGF-2 comprises several isoforms of different lengths including the most used forms with 146 amino acids (isoform 1 according to UniProt database, http://www.uniprot.org, SEQ ID NO:1) and 155 amino acids (isoform 3, SEQ ID NO:2), respectively (FIG. 1). When manufactured in E. coli, isoform 1 is expressed with an additional initiator methionine at its N-terminus, wherein the methionine is typically removed by proteolytic activities of E. coli. It is known that FGF-2 is highly labile at 37° C. which limits its usage in culturing of cells due to rapid loss of biological activity (Furue M. K. et al., Proc Natl Acad Sci USA 105: 13409-13414 (2008), Levenstein M. E. et al., Stem Cells 24: 568-574 (2006)). Heparin, sulfate ion, a number of polysulfated saccharides and heparin-mimicking polymer covalently conjugated to FGF-2 enhance the stability of FGF-2 against thermal denaturation (Shahrokh Z. et al., in: Formulation and Delivery of Proteins and Peptides by Cleland J. L. and Langer R., ACS Symposium Series, Vol. 567, Chapter 6, pp 85-99 (1994); Nguyen T. H. et al., Nature Chemistry 5: 221-227 (2013)).

FGF-2 contains four cysteine residues of which two are surface-exposed and the other two are buried within the protein. Depending on the numbering scheme, the surface-exposed cysteines are at positions 69 and 87 (SEQ ID NO:1), positions 70 and 88 (SEQ ID NO:1 plus the initiator methionine), or positions 78 and 96 (SEQ ID NO:2). The cysteines could form disulfide bridges which may generate disulfide-linked homodimers of FGF-2 which have been described to dissociate to unfolded monomers via spontaneous thiol-disulfide exchange, resulting in aggregation and precipitation (Shahrokh Z. et al., in: Formulation and Delivery of Proteins and Peptides by Cleland J. L. and Langer R., ACS Symposium Series, Vol. 567, Chapter 6, pp 85-99 (1994)).

Recombinant wild-type FGF-2 can be expressed in E. coli in a soluble, active form. Purification of FGF-2 from cell suspension can be conducted by standard chromatographic steps such as heparin affinity chromatography and ion exchange chromatography. The biological activity can be determined by cell-based assays using FGF-2 sensitive cells which, for example, proliferate in the presence of FGF-2.

WO2003/094835 disclosed FGF-2 variants with enhanced receptor subtype specificity. A mutated FGF-2 protein (based on isoform 3) designated "FGF2(3,5Q)-N111G" with the amino acid exchanges A3Q+S5Q+N111G showed an increase in mitogenicity on FGF receptor-1 and FGF receptor-3IIIc (expressing) cells.

U.S. Pat. No. 6,083,706 disclosed methods of inhibiting the export of a leaderless protein such as FGF-2 from a cell expressing the protein. In this context, mutated FGF-2 proteins (based on isoform 3) with the amino acid exchanges C78S and C96S are disclosed. U.S. Pat. No. 6,083,706 does not teach if these mutations have an effect on protein stability or activity.

EP1444995 disclosed the use of animal or human basic fibroblast growth factor (FGF-2) derived proteins for the preparation of biomaterials or medical devices chosen among endovascular prostheses, such as stents and bypass grafts, or coated endoprostheses, or other kinds of medical prostheses, said FGF-2 derived proteins being chosen among FGF-2 mutants which are unable to interact specifically with the Translokin. The amino acid exchange Q65S is disclosed as it is used in one FGF-2 mutant (based on isoform 3) having the mutation combination of Q65S+E68S+R69V+V71E+S73Y.

WO2013090919 disclosed the amino acid exchange K128N in isoform 3, wherein the FGF-2 K128N mutant exhibits increased thermostability relative to wild-type FGF-2, allowing for methods of culturing human pluripotent stem cells in the presence of lower levels of FGF-2 K128N relative to wild-type FGF-2.

Seno M. et al. (Biochem Biophys Res Commun 151: 701-708 (1988)) disclosed the single mutants C70S and C88S in isoform 1 of FGF-2 wherein the biological activity and heparin binding ability was retained when the serine was substituted for the cysteine residue at either 70 or 88 of the FGF-2 protein. This finding indicates that the cysteines at these positions are not essential for expressing biological activity.

Fox G. M. et al. (J Biol Chem 263: 18452-184528 (1988)) disclosed the double mutant C70S+C88S of the FGF-2 protein (isoform 1). This double mutant and natural sequence bovine and human forms were equally active in all assays.

Heath W. F. et al. (Biochemistry 30: 5608-5615 (1991)) disclosed the double mutant C69A+C87S of the FGF-2 protein (isoform 1). Recombinant human FGF-2 (isoform 1) wild-type protein and the double mutant C69A+C87S, an analogue where two of the four cysteines had been replaced by alanine and serine, were equipotent to standard bovine basic fibroblast growth factor.

Arakawa T. et al. (Biochem Biophys Res Commun 161: 335-341 (1989)) disclosed a mutant FGF-2 protein in which all four cysteines were replaced by serine. It exhibited mitogenic activity on NIH 3T3 cells which was indistinguishable from the natural sequence molecule.

Rinas U. et al. (Biotechnology (NY) 10: 435-440 (1992)) disclosed mutated FGF-2 proteins (isoform 1) with the single mutation C70S and the double mutation C70S+C88S. Both the single mutation at position 88 and the double mutation at positions 70 and 88 do not greatly alter the partition of bFGF (FGF-2) into soluble and insoluble cell fractions. Thermal stability experiments at 42° C. and 70° C. revealed that cysteine to serine substitutions did not cause aggregation of the folded protein in vitro. No differences in the biological activity of these mutants compared to wild-type FGF-2 were reported.

Caccia P. et al. (Eur J Biochem. 204: 649-655 (1992)) disclosed derivatives of FGF-2 proteins, isoform 3, with chemically modified sulfhydryl groups. Among these, treatment of FGF-2 with iodoacetic acid led to the isolation of a partially carboxymethylated form (Cm-FGF). Peptide mapping analysis of the modified protein showed that two cysteines (78 and 96) were blocked by a carboxymethyl group. Cm-FGF was more stable than the unmodified molecule as measured by HPLC and SDS/PAGE analysis, and more active than unmodified FGF-2 in stimulating proliferation.

US20120225479 disclosed engineered FGF2 molecules with increased thermostability compared to the wild-type protein. The wild-type FGF-2 lost half of its activity when stored at 37° C. in serum-free culture medium for 2 hours and 90% of its activity after 24 hours. The Q65I+N111G+C96S FGF-2 mutant had a 10-fold improvement in thermostability in repeated cell based assays. The combination of Q65I+N111G+C96S mutations increased the expression level of the protein in human cells compared to the wild-type protein. US20120225479 does not teach how a thermostable FGF-2 polypeptide with an increased biological activity, compared to wild-type FGF-2, can be generated.

As mentioned above, FGF-2 is highly labile at 37° C. which limits its usage for example in culturing of cells due to rapid loss of biological activity. Therefore, there is a need in the art for improved FGF-2 polypeptides.

All references cited herein, including patent applications and publications, are incorporated by reference in their entirety.

SUMMARY OF THE INVENTION

Several muteins of FGF-2 protein and the wild-type FGF-2 protein were recombinantly expressed, purified, and analyzed. Surprisingly, it was found that three muteins not only show a higher thermostability and a higher stability to proteases than the wild-type protein, but also a higher biological activity. A mutein having five amino acid substitutions (called herein 5x-mutein_mb) showed the highest biological activity which was about 3.5-fold higher than for the wild-type FGF-2. Unexpectedly, the mutein with five amino acid substitutions (5x-mutein_mb) was nearly 2-fold more active than the mutein with three amino acid substitutions (called herein 3x-mutein_mb), wherein the only difference between these two muteins is the substitution of both surface-exposed cysteines to serine residues in the 5x-mutein. In the art it was known that exchange of surface-exposed cysteines does not affect the biological activity of FGF-2. Notably, no increase in biological activity has been described in the art when these cysteine residues were replaced. It was also unexpected that the mutein with four amino acid substitutions (called herein 4x-mutein_mb) was about 60% more active than the mutein with three amino acid substitutions (3x-mutein_mb), wherein the only differ- ence between these two muteins is the substitution of alanine-75 to cysteine in the 4x-mutein.

BRIEF DESCRIPTION OF THE DRAWINGS

FIG. 1 shows amino acid sequences of wild-type FGF-2 proteins isoform 1 ("WT-isoform-1" (SEQ ID NO:1)) and isoform 3 ("WT-isoform-3" (SEQ ID NO:2)). Asterisks ("*") mark identical amino acid residues for both proteins at the same position. The numbers designate the particular position of the last amino acid in a line.

FIG. 2 shows amino acid sequences of wild-type FGF-2 proteins isoform 1 ("WT-isoform-1" (SEQ ID NO:1)) and the FGF-2 muteins of the present invention ("2x-mutein_mb" (SEQ ID NO:3), "3x-mutein_mb" (SEQ ID NO:4), "4x-mutein_mb" (SEQ ID NO:5) and "5x-mutein_mb" (SEQ ID NO:6)). Asterisks ("*") mark identical amino acid residues for all proteins at the same position. Dots (".") and colons (":") mark positions where at least one sequence contains another amino acid, but the amino acids of all sequences at this position are structurally related, for example serine and cysteine. The numbers designate the particular position of the last amino acid in a line.

Figure 7:
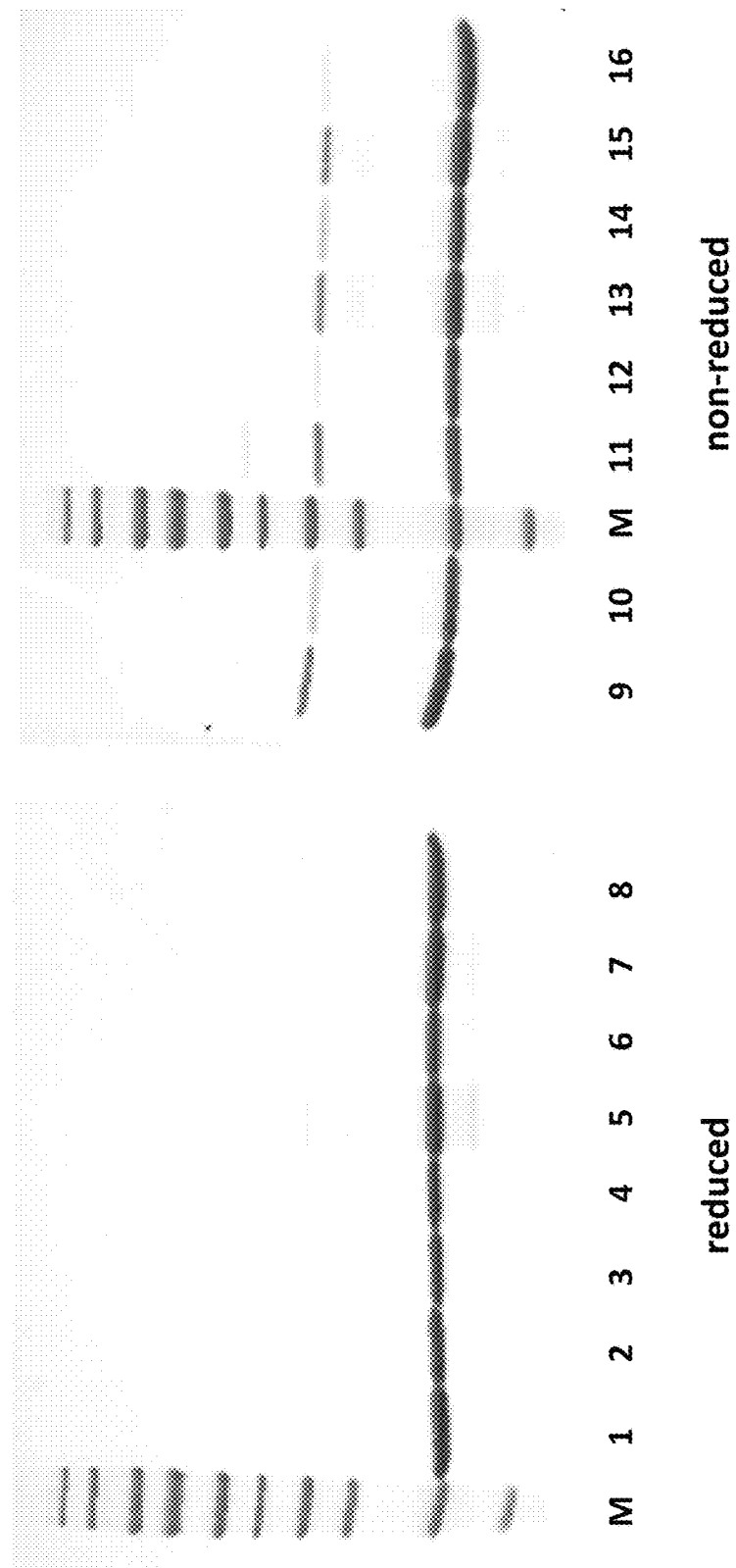

FIG. 7: Thermostability of wild-type FGF-2 protein ("WT-isoform-1") and the muteins of the present invention ("3x-mutein_mb", "4x-mutein_mb" and "5x-mutein_mb") at 37° C., analyzed by reducing and non-reducing SDS PAGE. The proteins were subjected to incubation at 37° C. in a buffered solution for 3 days. Samples were taken before the incubation and on day 3. 20 µL, of each protein solution (+/−2-mercaptoethanol) was applied to the SDS gel, which was stained with Coomassie. M: molecular weight marker with marker sizes of 170, 130, 100, 70, 55, 40, 35, 25, 15, 10 kDa (from top to bottom). WT-isoform-1: lanes 1, 2, 9, 10. 3x-mutein_mb: lanes 5, 6, 13, 14. 4x-mutein_mb: lanes 7, 8, 15, 16. 5x-mutein_mb: lanes 3, 4, 11, 12. Before incubation at 37° C.: lanes 1, 3, 5, 7, 9, 11, 13, 15. After 3 day incubation at 37° C.: lanes 2, 4, 6, 8, 10, 12, 14, 16. Reducing conditions: lanes 1-8. Non-reducing conditions: lanes 9-16.

Figure 8:
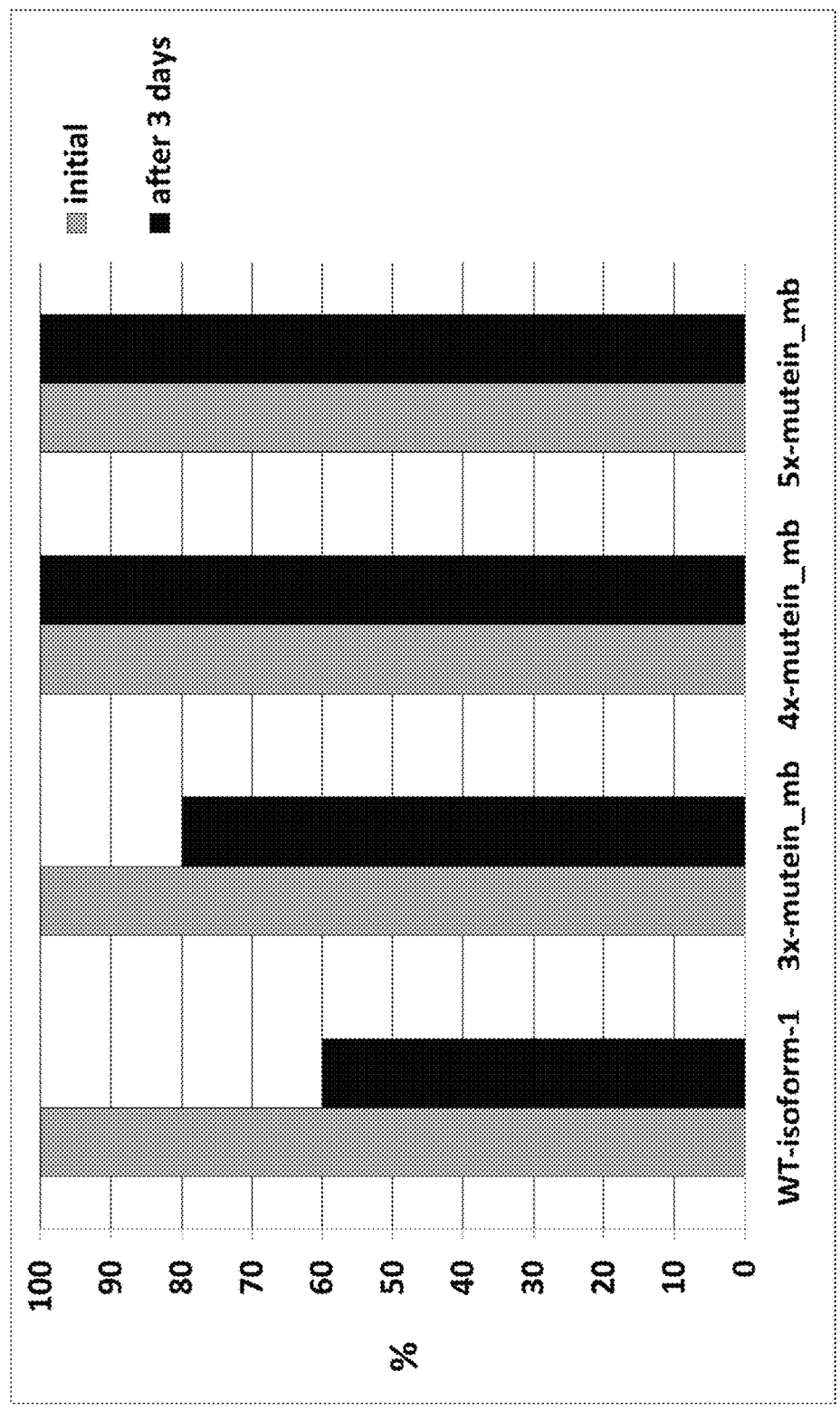

FIG. 8 shows graphical representation of thermostability of wild-type FGF-2 protein ("WT-isoform-1") and the muteins of the present invention ("3x-mutein_mb", "4x-mutein_mb" and "5x-mutein_mb") at 37° C. The amount of each monomeric FGF-2 protein before the incubation at 37° C., as visualized by the 15 kDa band in the Coomassie-stained SDS gel of FIG. 7, was set to 100%. The amount of each monomeric FGF-2 protein after the 3 day incubation at 37° C., as visualized by the 15 kDa band in the Coomassie-stained SDS gel of FIG. 7, was calculated as percent of the initial amount before incubation.

Figure 9:
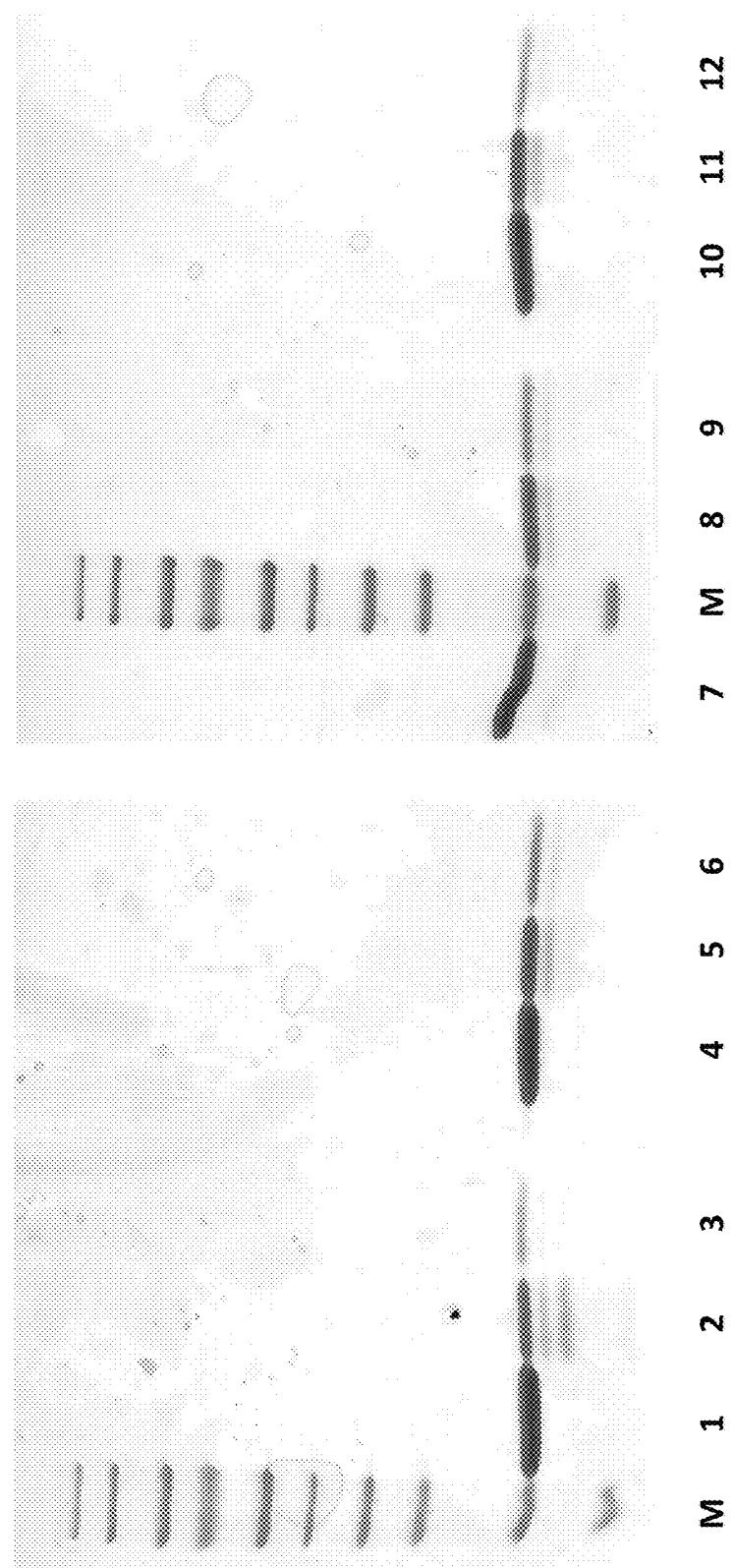

FIG. 9 shows SDS PAGE of trypsin-incubated FGF-2 polypeptides. Wild-type FGF-2 protein ("WT-isoform-1") and the muteins of the present invention ("3x-mutein_mb", "4x-mutein_mb" and "5x-mutein_mb") were incubated with trypsin for 80 minutes. Samples were taken before the addition of trypsin and after 30 and 80 minutes. 20 µL, of each protein was applied to the SDS gel, which was stained with Coomassie. M: molecular weight marker with marker sizes of 170, 130, 100, 70, 55, 40, 35, 25, 15, 10 kDa (from top to bottom). WT-isoform-1: lanes 1, 2, 3. 3x-mutein_mb: lanes 7, 8, 9. 4x-mutein_mb: lanes 10, 11, 12. 5x-mutein_mb: lanes 4, 5, 6. Before incubation with trypsin: lanes 1, 4, 7, 10. 30 minutes incubation with trypsin: lanes 2, 5, 8, 11. 80 minutes incubation with trypsin: lanes 3, 6, 9, 12.

Figure 10:
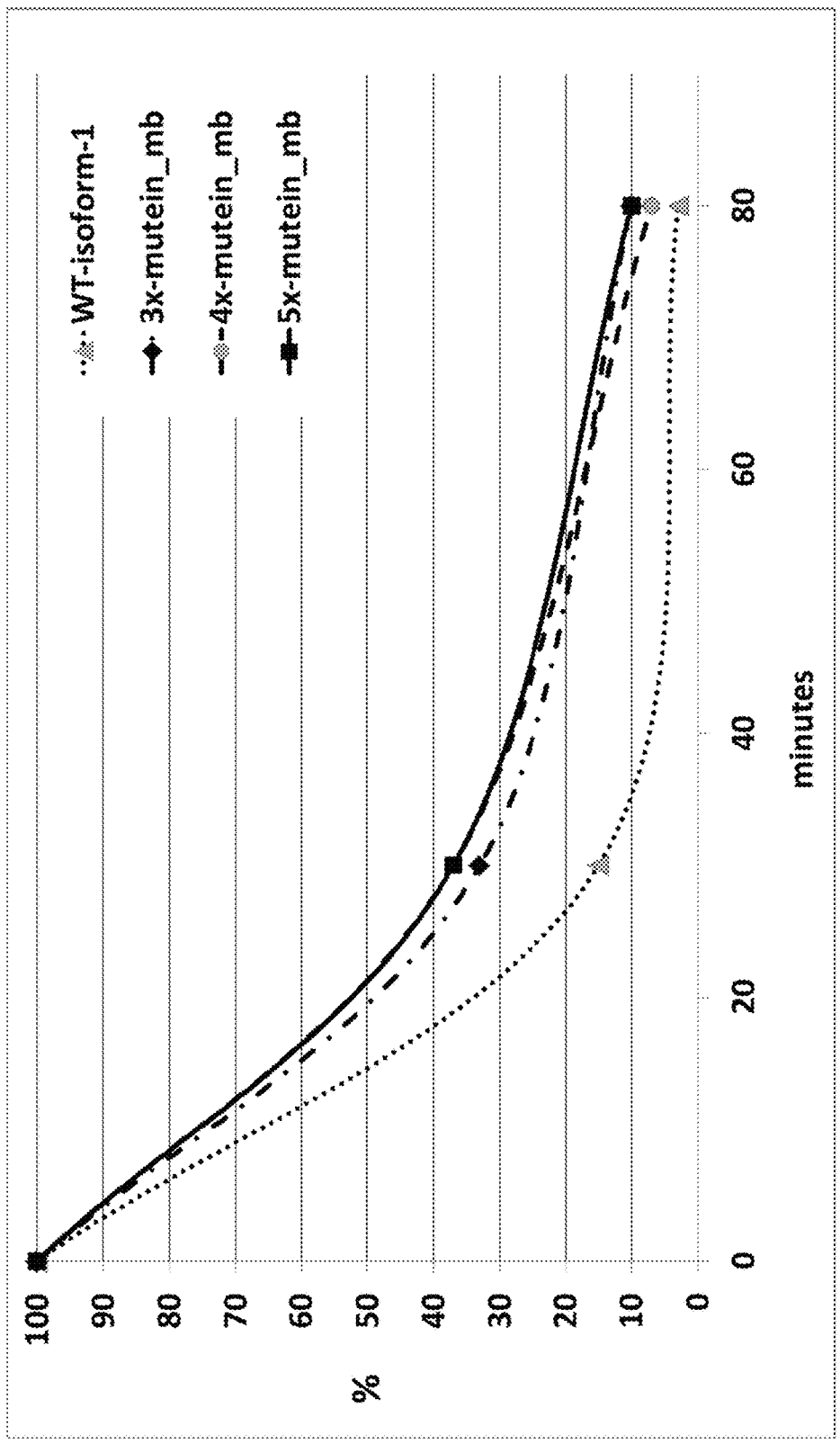

FIG. 10 shows graphical representation of stability of FGF-2 polypeptides to trypsin. The amount of each monomeric FGF-2 protein before the incubation with trypsin, as visualized by the undegraded (intact) 15 kDa band in the Coomassie-stained SDS gel of FIG. 9, was set to 100%. The amount of each undegraded (intact) FGF-2 protein after 30 and 80 minutes of incubation with trypsin, as visualized by the 15 kDa band in the Coomassie-stained SDS gel of FIG. 9, was calculated as percent of the initial amount before incubation.

Figure 11:
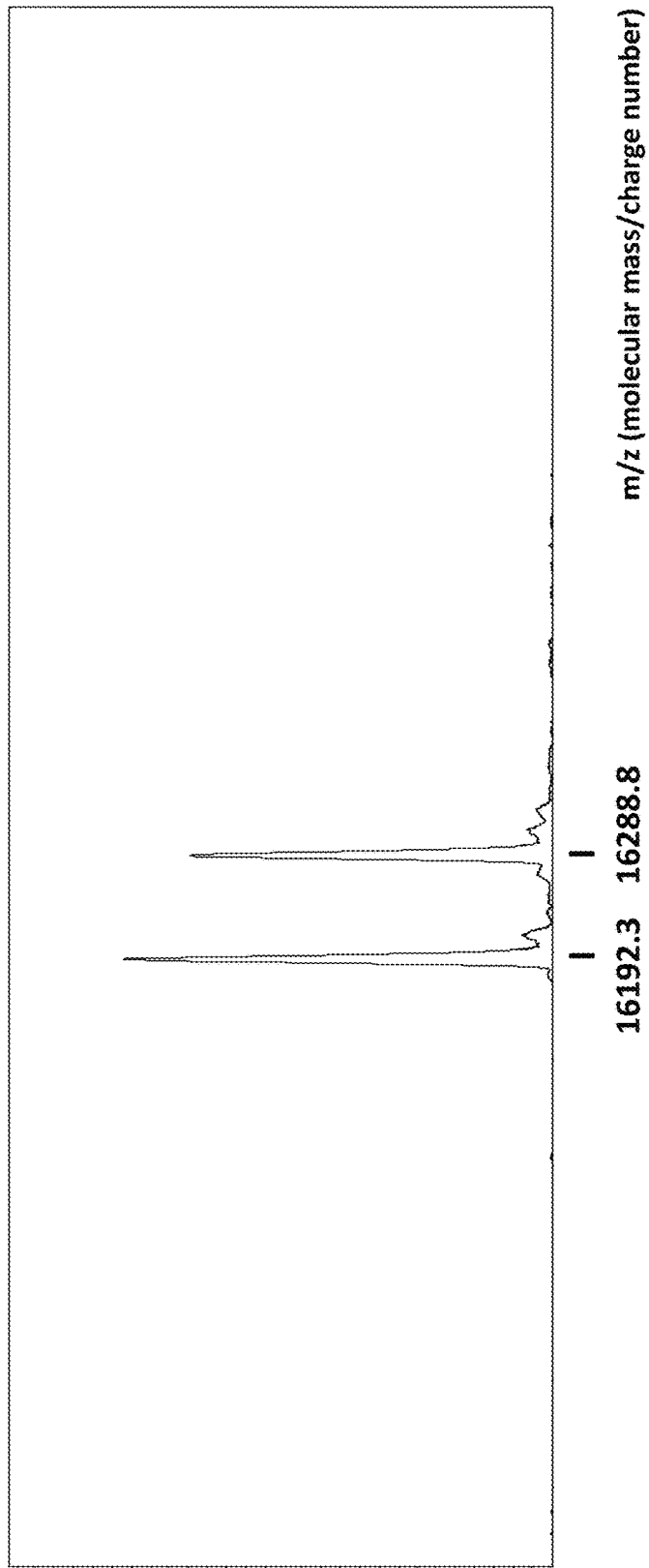

FIG. 11 shows mass spectrometry analysis of 5x-mutein_mb. Purified 5x-mutein_mb was analyzed by electrospray ionization mass spectrometry (ESI-MS).

DETAILED DESCRIPTION OF THE INVENTION

For the numbering of amino acid residues in the FGF-2 muteins of the present invention, it is used the numbering of SEQ ID NO:1 (WT-isoform-1), which is the isoform 1 of FGF-2 according to the UniProt database (www.uniprot.org). Equivalent positions of other isoforms of FGF-2 can be calculated. For example, for isoform 3 of FGF-2 (SEQ ID NO:2), the positions are shifted by 9 amino acid residues relative to isoform 1.

Depending on the expression system, recombinant proteins may contain an initiator methionine residue on its N-terminus. For the FGF-2 polypeptides of the present invention, variants with and without such a methionine residue are useful. Preferentially, an FGF-2 polypeptide does not have an artificial N-terminal methionine residue which is also not present in the natural form of FGF-2.

Surprisingly it was found that a fibroblast growth factor-two (FGF-2) polypeptide that differs from the wild-type FGF-2 (SEQ ID NO:1) at least at amino acid positions 56, 102 and 119, wherein the differences are Q56I, N102G and K119N substitutions leads firstly to a biological more active FGF-2 polypeptide than the wild-type FGF-2 polypeptide, secondly to a more thermostable FGF-2 polypeptide than the wild-type FGF-2 polypeptide and thirdly to a more protease-resistant FGF-2 polypeptide than the wild-type FGF-2 polypeptide. The synergistic effect of a higher biological activity, an increased thermostability and an increased resistance to proteolytic degradation results in a superior FGF-2 polypeptide, compared to the wild-type FGF-2 polypeptide, which may be used for example in cell culture media.

An FGF-2 polypeptide of said amino acid substitutions (Q56I, N102G and K119N; the 3x-mutein) has a biological activity which is at least 1.5-fold higher than the wild-type FGF-2 polypeptide incubated under the same conditions (example 8).

After incubation for 3 days at 37° C. in a buffered solution, the amount of a said 3x-mutein FGF-2 polypeptide is at least 20% higher than for wild-type FGF-2 polypeptide incubated under the same conditions (example 9).

Said 3x-mutein FGF-2 polypeptide is more stable to proteolytic degradation than the wild-type FGF-2 polypeptide. Trypsin is an endopeptidase which cleaves peptide sequences after basic residues and can be used as model protease to analyze the stability of proteins to proteolytic degradation. Tryptic activities are also often present under cell culture conditions. Therefore, a higher stability to proteases may increase the half-life of a FGF-2 polypeptide in cell culture. After incubation with trypsin at a ratio of 1:8 (trypsin:FGF-2) for 30 minutes at 37° C. in solution, the amount of said 3x-mutein FGF-2 polypeptide is at least 1.5-fold higher than for wild-type FGF-2 polypeptide incubated under the same conditions (example 10).

Therefore, in one aspect the present invention provides a fibroblast growth factor-two (FGF-2) polypeptide that differs from the wild-type FGF-2 (SEQ ID NO:1) at least at amino acid positions 56, 102 and 119, wherein the differences are Q56I, N102G and K119N substitutions.

Said 3x-mutein FGF-2 polypeptide may have the sequence of SEQ ID NO:4 (3x-mutein_mb).

Surprisingly it was found that a fibroblast growth factor-two (FGF-2) polypeptide that differs from the wild-type FGF-2 (SEQ ID NO:1) at least at amino acid positions 56, 75, 102 and 119, wherein the differences are Q56I, A75C, N102G and K119N substitutions leads firstly to a biological more active FGF-2 polypeptide than the wild-type FGF-2 polypeptide, secondly to a more thermostable FGF-2 polypeptide than the wild-type FGF-2 polypeptide and thirdly to a more protease-resistant FGF-2 polypeptide than the wild-type FGF-2 polypeptide. The synergistic effect of a higher biological activity, an increased thermostability and an increased resistance to proteolytic degradation results in a superior FGF-2 polypeptide compared to the wild-type FGF-2 polypeptide which may be used for example in cell culture media.

An FGF-2 polypeptide of said amino acid substitutions (Q56I, A75C, N102G and K119N; the 4×-mutein) has a biological activity which is at least 2-fold higher than the wild-type FGF-2 polypeptide incubated under the same conditions (example 8).

After incubation for 3 days at 37° C. in a buffered solution, the amount of a said 4×-mutein FGF-2 polypeptide is at least 40% higher than for wild-type FGF-2 polypeptide incubated under the same conditions (example 9). Said 4×-mutein FGF-2 polypeptide is more stable to proteolytic degradation than the wild-type FGF-2 polypeptide. After incubation with trypsin at a ratio of 1:8 (trypsin:FGF-2) for 30 minutes at 37° C. in solution, the amount of said 4×-mutein FGF-2 polypeptide is at least 2-fold higher than for wild-type FGF-2 polypeptide incubated under the same conditions (example 10). Therefore, in one aspect the present invention provides a fibroblast growth factor-two (FGF-2) polypeptide that differs from the wild-type FGF-2 (SEQ ID NO:1) at least at amino acid positions 56, 75, 102 and 119, wherein the differences are Q56I, A75C, N102G and K119N substitutions. Said 4×-mutein FGF-2 polypeptide may have the sequence of SEQ ID NO:5 (4×-mutein_mb).

Surprisingly it was found that a fibroblast growth factor-two (FGF-2) polypeptide that differs from the wild-type FGF-2 (SEQ ID NO:1) at least at amino acid positions 56, 69, 87, 102 and 119, wherein the differences are Q56I, C69S, C87S, N102G and K119N substitutions leads firstly to a biological more active FGF-2 polypeptide than the wild-type FGF-2 polypeptide, secondly to a more thermostable FGF-2 polypeptide than the wild-type FGF-2 polypeptide and thirdly to a more protease-resistant FGF-2 polypeptide than the wild-type FGF-2 polypeptide. The synergistic effect of a higher biological activity, an increased thermostability and an increased resistance to proteolytic degradation results in a superior FGF-2 polypeptide which may be used for example in cell culture media.

An FGF-2 polypeptide of said amino acid substitutions (Q56I, C69S, C87S, N102G and K119N; the 5×-mutein) has a biological activity which is at least 2-fold higher than the wild-type FGF-2 polypeptide incubated under the same conditions (example 8).

After incubation for 3 days at 37° C. in a buffered solution, the amount of a said 5×-mutein FGF-2 polypeptide is at least 40% higher than for wild-type FGF-2 polypeptide incubated under the same conditions (example 9).

After incubation for 5 days at 37° C. in a buffered solution, the specific activity of a said 5×-mutein FGF-2 polypeptide is at least 2-fold, preferentially at least 4-fold, most preferentially at least 6-fold higher than for wild-type FGF-2 polypeptide incubated under the same conditions (example 9).

After incubation for 5 days at 37° C. in a buffered solution, the specific activity of a said 5×-mutein FGF-2 polypeptide is at least 50%, preferentially at least 75%, most preferentially at least 90% of the specific activity of that said 5×-mutein FGF-2 polypeptide before incubation (example 9).

Said 5×-mutein FGF-2 polypeptide is more stable to proteolytic degradation than the wild-type FGF-2 polypeptide. After incubation with trypsin at a ratio of 1:8 (trypsin:FGF-2) for 30 minutes at 37° C. in solution, the amount of said 5×-mutein FGF-2 polypeptide is at least 2-fold higher than for wild-type FGF-2 polypeptide incubated under the same conditions (example 10). Therefore, in one aspect the present invention provides a fibroblast growth factor-two (FGF-2) polypeptide that differs from the wild-type FGF-2 (SEQ ID NO:1) at least at amino acid positions 56, 69, 87, 102 and 119, wherein the differences are Q56I, C69S, C87S, N102G and K119N substitutions. Said 5×-mutein FGF-2 polypeptide may have the sequence of SEQ ID NO:6 (5×-mutein_mb).

In one aspect the present invention provides nucleic acids encoding said 3×-mutein, 4×-mutein or 5×-mutein FGF-2 polypeptides. In a preferred embodiment the nucleic acids encode said FGF-2 polypeptides having the sequence of SEQ ID NO:4, SEQ ID NO:5 or SEQ ID NO:6.

In one aspect the present invention provides a host cell expressing said 3×-mutein, 4×-mutein or 5×-mutein FGF-2 polypeptide. In a preferred embodiment the host cell expresses the FGF-2 polypeptide having the sequence of SEQ ID NO:4, SEQ ID NO:5 or SEQ ID NO:6.

An FGF-2 polypeptide of the present invention may be present in a liquid solution or in a solid form. The solid form may comprise, for example, substances which are able to form matrices in a dried format. The FGF-2 polypeptide may be bound on the surface of such a matrix or incorporated into the matrix.

An FGF-2 polypeptide of the present invention may be used in combination with a liquid, semisolid and solid cell culture medium to promote, for example, cell growth, cell differentiation and cell migration, and to keep cells in an undifferentiated state. Preferred cells to be cultured are affected by said FGF-2 polypeptide and comprise but are not limited to pluripotent cells, mesenchymal stem cells, bone marrow stromal cells and neural stem cells. The FGF-2 polypeptide of the present invention may be part of a "ready-to-use" medium; in this case, the FGF-2 polypeptide of the present invention may be present in the medium in a concentration of 1-2,000 ng/mL, more preferred in a concentration of 1-200 ng/mL and most preferred in a concentration of 4-100 ng/mL.

An FGF-2 polypeptide of the present invention may be used in combination with a label which allows the detection of FGF-2. Such labels comprise but are not limited to fluorophores and quantum dots. The label may be attached directly to the FGF-2 polypeptide by for example chemical linkage. In another embodiment, the label may be indirectly attached to the FGF-2 polypeptide wherein the label is attached to another molecule and this molecule binds to FGF-2 polypeptide or a modified variant thereof. One example for such an indirect label is the biotinylation of an FGF-2 polypeptide and addition of a biotin-binding protein which is conjugated to a fluorophor.

In one aspect the present invention provides a method for culturing FGF-2 sensitive cells in a cell culture medium, the method comprises the step of cultivation of FGF-2 sensitive cells, wherein said medium comprises an FGF-2 polypeptide according to the present invention. The FGF-2 polypeptide may be a 3×-mutein, a 4×-mutein or a 5×-mutein FGF-2 polypeptide. Preferentially, the FGF-2 polypeptide may be an FGF-2 polypeptide having the sequence of SEQ ID NO:4, SEQ ID NO:5 or SEQ ID NO:6.

The FGF-2 sensitive cells may be any cell which is affected by the presence of FGF-2. Preferentially, the FGF-2 sensitive cells may be selected from the group consisting of pluripotent cells, embryonic stem cells, induced pluripotent stem cells, mesenchymal stem cells, bone marrow stromal cells and neural stem cells.

Due to the effects of the FGF-2 polypeptides of the present invention as described herein the FGF-2 polypeptides of the present invention are more stable in the cell culture medium leading to the reduction of the frequency of addition of FGF-2 to the cell culture and/or to a reduced amount of FGF-2 which has to be added to the cell culture.

In a preferred embodiment of the invention, the method for culturing FGF-2 sensitive cells in a cell culture medium comprises the step of culturing FGF-2 sensitive cells, wherein said medium comprises an FGF-2 polypeptide according to the present invention, wherein said method comprises the additional step of reiterate adding an FGF-2 polypeptide according to the present invention to said medium for maintenance of a constant concentration of said FGF-2 polypeptide in said medium during the cell culturing process. The frequency of said reiterate adding of an FGF-2 polypeptide according to the present invention may be reduced at least for the factor 1.5, more preferentially at least for the factor 2, most preferentially at least for the factor 2.5 compared to the corresponding reiterate adding of wild-type FGF-2 polypeptide to the medium during the cell culturing process which is necessary for maintenance of the same constant concentration of FGF-2 polypeptide.

In a preferred embodiment of the invention, the method for culturing FGF-2 sensitive cells in a cell culture medium comprises the step of culturing FGF-2 sensitive cells, wherein said medium comprises an FGF-2 polypeptide according to the present invention, wherein the amount of said FGF-2 polypeptide is reduced compared to the amount of wild-type FGF-2 polypeptide. Said reduction of the amount may be at least for the factor 1.5, more preferentially at least for the factor 2, most preferentially at least for the factor 2.5, compared to the corresponding amount of wild-type FGF-2 polypeptide in the medium during the cell culturing process.

In a preferred embodiment of the invention, the method for culturing FGF-2 sensitive cells in a cell culture medium comprises the step of culturing FGF-2 sensitive cells, wherein said medium comprises an FGF-2 polypeptide according to the present invention, wherein the amount of said FGF-2 polypeptide is reduced compared to the amount of wild-type FGF-2 polypeptide, and wherein said method comprises the additional step of reiterate adding said FGF-2 polypeptide to said medium for maintenance of a constant concentration of said FGF-2 polypeptide in said medium during the cell culturing process. Said reduction of the amount may be at least for the factor 1.5, more preferentially at least for the factor 2, most preferentially at least for the factor 2.5, compared to the corresponding amount of wild-type FGF-2 polypeptide in the medium during the cell culturing process. The frequency of said reiterate adding of an FGF-2 polypeptide according to the present invention may be reduced at least for the factor 1.5, more preferentially at least for the factor 2, most preferentially at least for the factor 2.5 compared to the corresponding reiterate adding of wild-type FGF-2 polypeptide to the medium during the cell culturing process.

In one aspect of the present invention a cell culture medium for culturing of FGF-2 sensitive cells comprising an FGF-2 polypeptide of the present invention is provided. The concentration may be lower than the concentration used in medium comprising wild-type FGF-2 due to the effects as described herein. For example, the concentration of the wild-type FGF-2 polypeptide in a cell culture medium may be in the range of 20-40 ng/mL. Then the concentration of an FGF-2 polypeptide of the present invention may be in the range of 13.3-16.7 ng/mL, more preferred in the range of 10-20 ng/mL, and most preferred be in the range of 8-16 ng/mL.

In one aspect of the present invention, FGF-2 polypeptides of other mammalian species than human with higher thermostability, higher biological activity and higher stability to proteases can be generated. For example, the identity of human FGF-2 polypeptide to FGF-2 polypeptides of other mammalian species based on the amino acid sequence is: 96.6% for murine FGF-2 (Uniprot entry P15655), 96.6% for rat FGF-2 (Uniprot entry P13109), 98.6% for bovine FGF-2 (Uniprot entry P03969), 97.9% for sheep FGF-2 (Uniprot entry P20003), 93.2% for opossum FGF-2 (Uniprot entry P48798) and 100% for chimpanzee FGF-2 (Uniprot entry Q5IS69). Due to the high degree of identity, the amino acid substitutions of the present invention, as disclosed for the generation of a human FGF-2 3x-mutein, 4x-mutein and 5x-mutein, can be transferred to other mammalian FGF-2 polypeptides using the corresponding substitutions to generate other mammalian FGF-2 polypeptides with higher thermostability, higher biological activity and higher stability to proteases.

Definitions

As used herein, "FGF-2" refers to human fibroblast growth factor-2 as described in the Uniprot database, http://www.uniprot.org. If not stated otherwise, the term "FGF-2" designates the FGF-2 protein/FGF-2 polypeptide.

As used herein, the terms "protein" and "polypeptide" refer to a peptide sequence of at least 10 amino acid residues length. The terms "FGF-2 polypeptide" and "FGF-2 protein" as used herein have the same meaning and are used interchangeably. Both terms comprise a full-length version of wild-type or mutein FGF-2 or a truncated wild-type or mutein FGF-2 which has at least 10%, 20%, 30%, 40%, 50%, 60%, 70%, 80%, 90%, 95%, 99% of the biological activity compared to the corresponding full-length form. The FGF-2 may be a chemically modified FGF-2 protein, wherein such modifications comprise for example N-formylation, oxidation, deamidation, isomerization, decarboxylation, phosphorylation, glycosylation, lipidation, gluconylation, phosphogluconylation, hydroxylation, sulphation, methylation and carbamylation.

An isolated FGF-2 polypeptide of the present invention is an FGF-2 which was generated recombinantly in a host cell and which was isolated by the isolation methods well known in the art such as ion-exchange chromatography, affinity chromatography, hydrophobic interaction chromatography and size-exclusion chromatography.

As used herein, the term "fragment" is intended to include forms of a protein or a polypeptide which are truncated. A fragment of an FGF-2 mutein therefore refers to a portion of the sequence of a FGF-2 mutein, wherein the portion contains contiguous amino acids and has at least partial biological activity of the full-length protein as well as a higher thermostability than wild-type FGF-2. A fragment can be produced for example by proteolytic cleavage of a polypeptide or by recombinant expression of the fragment.

As used herein, the term "isoforms" refers to any of two or more functionally similar proteins or polypeptides that have a similar but not identical amino acid sequence and are either encoded by different genes or by RNA transcripts from the same gene which have different RNA sequences. As used herein, the isoforms of FGF-2 are referring to the definition as described in the Uniprot database, http://www.uniprot.org.

As used herein, the terms "cytokine" and "growth factor" both refer to proteins and polypeptides which are capable of inducing biological effects such as the stimulation of cellular growth, proliferation and cellular differentiation. Both terms are used interchangeable. Examples are interleukins, interferons, fibroblast growth factors, insulin and insulin-like growth factors, chemokines, colony-stimulating factors and tumor necrosis factors. Typically, cytokines and growth factors bind to cells via specific receptors. In some cases, they bind to specific receptors in a complexed form, such as IL-15 which can be first bound to IL-15 receptor alpha and then is trans-presentated to IL-15 receptor beta/gamma.

As used herein, the term "mutein" is intended to include proteins and polypeptides with an altered amino acid sequence and which arise as a result of a mutation or a recombinant DNA procedure. Examples include but are not restricted to substitution of at least one amino acid residue by another, deletion of at least one amino acid residue, insertion of at least one amino acid residue, and inversion of amino acid residues.

The term "3x-mutein" or "3x-mutein FGF-2" refers to an FGF-2 polypeptide that differs from the wild-type FGF-2 (SEQ ID NO:1) at least at amino acid positions 56, 102 and 119, wherein the differences are Q56I, N102G and K119N substitutions. A specific example for a 3x-mutein is the 3x-mutein_mb having the sequence of SEQ ID NO:4. Other examples for 3x-muteins comprise sequences which have the substitutions Q56I, N102G and K119N and also at least one further insertion, deletion or substitution which does not affect activity and thermostability of the FGF-2 polypeptide.

The term "4x-mutein" or "4x-mutein FGF-2" refers to an FGF-2 polypeptide that differs from the wild-type FGF-2 (SEQ ID NO:1) at least at amino acid positions 56, 75, 102 and 119, wherein the differences are Q56I, A75C, N102G and K119N substitutions. A specific example for a 4x-mutein is the 4x-mutein_mb having the sequence of SEQ ID NO:5. Other examples for 4x-muteins comprise sequences which have the substitutions Q56I, A75C, N102G and K119N and also at least one further insertion, deletion or substitution which does not affect activity and thermostability of the FGF-2 polypeptide.

The term "5x-mutein" or "5x-mutein FGF-2" refers to an FGF-2 polypeptide that differs from the wild-type FGF-2 (SEQ ID NO:1) at least at amino acid positions 56, 69, 87, 102 and 119, wherein the differences are Q56I, C69S, C87S, N102G and K119N substitutions. A specific example for a 5x-mutein is the 5x-mutein_mb having the sequence of SEQ ID NO:6. Other examples for 5x-muteins comprise sequences which have the substitutions Q56I, C69S, C87S, N102G and K119N and also at least one further insertion, deletion or substitution which does not affect activity and thermostability of the FGF-2 polypeptide.

As used herein, the term "wild-type" refers to a protein or polypeptide sequence which is the normal, non-mutated version common in nature, and which is stated as the reference sequence in the UniProt database (http://www.uniprot.org).

As used herein, the terms "thermostability" and "thermostable" refer to the characteristic of proteins and polypeptides which show an increased stability against thermal denaturation, compared to the original protein (such as a wild-type protein); therefore thermostable proteins are capable of being subjected to a moderate degree of heat without or only partial loss of characteristic properties. A thermostable mutein shows at least some biological activity at a certain temperature when the original or wild-type protein does not, and/or a thermostable mutein shows biological activity over a longer period than original or wild-type protein at a certain temperature. The remaining biological activity and the remaining amount of FGF-2 after thermal stressing can be used as measures for the thermostability of FGF-2 polypeptides.

Thermostability of proteins can also be analyzed by SDS polyacrylamide gel electrophoresis (SDS PAGE) of the proteins before and after incubation at a certain temperature. The amount of a thermostable protein at this temperature remains unaffected by the thermal incubation. However, the amount of a protein with a low level of thermostability decreases after thermal incubation when the incubation temperature results in protein unfolding, aggregation and/or precipitation.

As used herein, the term "ED50" refers to the half-maximal activity or effective dose of a protein or polypeptide in a cell-based assay. It is measured in ng protein per mL. The ED50 is generally referred to as "1 unit".

As used herein, the term "specific activity" refers to the biological activity of a protein or polypeptide per amount of the protein or polypeptide. It is measured in units per mg protein, U/mg. The specific activity [units/mg] can be calculated by the formula: specific activity [units/mg]=1E+06/ED50 [ng/mL]. The value of the specific activity strongly depends on the biological assay used for the determination of the ED50/specific activity.

As used herein, the term "calibrated specific activity" refers to the biological activity of a protein or polypeptide per amount of the protein or polypeptide, wherein the assay used to determine the ED50/specific activity is calibrated with a reference protein having a defined amount of units. The calibrated specific activity is measured in international units per mg protein, IU/mg, if the activity of reference protein is also given in IU; otherwise, it is measured in U/mg. Due to the calibration, the value of the specific activity does not depend on the biological assay used for the determination of the ED50/specific activity. Reference proteins for assay calibration can be obtained at the National Institute for Biological Standards and Control, NIBSC. In the case of FGF-2, the assigned activity of the reference protein 90/712 is given in IU/mg, and therefore calibrated specific activities of the FGF-2 muteins are also given in IU/mg.

As used herein, the term "cell culture medium" is intended to include liquid or gelatinous (semisolid and solid) substances comprising nutrients in which microorganisms, tissues or cells of any origin are cultivated. Various cell culturing liquid (media) known in the art of cell culturing (cell culturing process) can be used as stimulus for cells, including one or more of the following media DMEM, HBSS, DPBS, RPMI, Iscove's medium, X-VIVO™, each optionally supplemented e.g. with fetal calf serum, human serum or serum substitutes or other nutrients or cell stimuli like cytokines or small molecules. The media can be standard cell media like the above mentioned media or specialty media for e.g. primary human cell culture (e.g. for T cells, endothelial cells, hepatocytes or keratinocytes) or stem cells (e.g. hematopoietic expansion, mesenchymal stem cells). The media may contain supplements or reagents well known in the art, e.g. albumins and transport proteins, amino acids and vitamins, antibiotics, attachments factors, growth factors and cytokines, hormones or solubilizing agents. Various media are commercially available e.g. from LifeTechnologies or Sigma-Aldrich.

The term "reiterate adding an FGF-2 polypeptide to the medium for maintenance of a constant range of a concentration of said FGF-2 polypeptide in the medium during the cell culturing process" means that the range of the concentration of FGF-2 in a cell culture medium should be kept at a level with as less as deviation of the FGF-2 concentration in the medium as possible. It is known that FGF-2 is highly labile at 37° C., standardly the cell culture temperature, which limits its usage in culturing of cells due to rapid loss of biological activity. Due to this instability of FGF-2 in cell culture media, FGF-2 is added at several time points during the cell culture process to refill the FGF-2 concentration in the media and to keep the level of FGF-2 in said constant range. The level of FGF-2 should be sufficiently high for affecting the FGF-2 sensitive cells (effective amount). The effective amount is the amount required to achieve a desired effect triggered by FGF-2 on FGF-2 sensitive cells. The level (amount) decreases over the time due to the instability of FGF-2 in the medium. To avoid high deviations, the refilling of FGF-2 to the medium is necessary. The frequency of adding (refilling) FGF-2 to the medium can be reduced if an FGF-2 variant is more stable than the wild-type FGF-2 at 37° C. Such more stable FGF-2 variants are the FGF-2 polypeptides of the present invention. The term "corresponding reiterate adding of wild-type FGF-2 polypeptide to the medium during the cell culture process" means in this context the frequency of adding (refilling) wild-type FGF-2 to the medium which is necessary for maintenance of the same constant range of the concentration of FGF-2 as used for the FGF-2 polypeptides of the present invention. Due to the higher instability of wild-type FGF-2 in the cell culture medium, the frequency of adding of wild-type FGF-2 to the medium has to be higher than if FGF-2 of the present invention is used. The term "reiterate adding" refers to at least one additional adding of the substance, i.e. the FGF-2, to the medium wherein the medium comprises FGF-2 which may be degraded, denaturated, unfolded and/or rendered biologically inactive to a certain degree due to the instability of wild-type FGF-2 in cell culture media.

The term "FGF-2 sensitive cells" as used herein refers to cells which react to or are affected by the cytokine FGF-2, wherein FGF-2 induces biological effects as defined by the terms "cytokine" and "growth factor", i.e. these cells are dependent on FGF-2 for inducing biological effects such as the stimulation of cellular growth, proliferation and cellular differentiation (FGF-2 dependent cells). The cells may origin from any mammalian or human source, such as tumor, blood, tissue, bone marrow or cell lines, for example one or more cell types selected from the group consisting of human cells, fibroblasts, embryonic stem cells, keratinocytes, melanocytes, mesenchymal stem cells, epithelial cells, T-cells, regulatory T-cells, B-cells, NK-cells, NKT-cells, neuronal cells, dendritic cells, stem cells (adult, embryonic, hematopoietic), cells originating from epithelium, ectoderm, endoderm, endothelium, mesoderm, epithelial tissue, basal lamina, vasculature, connective tissue, fibrous tissues, muscle tissue, visceral or smooth muscle, skeletal muscle, cardiac muscle, nervous tissue, brain, spinal cord, cranial nerves, spinal nerves or motor neurons.

The term "host cell" means any cell of any organism that is selected, modified (e.g. genetically modified), transformed, grown, used or manipulated in any way, for the production of a substance by the cell, for example the expression by the cell of a gene, a DNA or RNA sequence, a protein or an enzyme.

As used herein, the terms "plasmid" and "vector" both refer to a double-stranded generally circular DNA sequence that is capable of automatically replicating in a host cell. Both terms are used interchangeable.

As used herein, the term "expression vector" refers to a vector/plasmid comprising a DNA sequence which is coding for a protein or polypeptide, wherein this protein or polypeptide can be produced, for example, in a cellular host by recombinant expression, or using a cell-free protein expression technology. Usually, an expression vectors comprises a promoter and a terminator sequence for the gene-of-interest, an origin-of-replication and a gene coding for a resistance marker such as an antibiotic. The expression of the protein or polypeptide may be regulated by an inducible promoter using inducers such as isopropyl β-D-1-thiogalactopyranoside (IPTG) or lactose.

As used herein, the term "synthetic gene" refers to double-stranded DNA coding for a protein or polypeptide, wherein the DNA has been generated by synthetic methods. Examples for such methods comprise chemical synthesis and oligonucleotide ligation. The codon usage can be optimized to match host capabilities and therefore to increase the level of recombinant protein expressed, wherein the protein is encoded by the synthetic gene.

As used herein, the terms "soluble protein" and "soluble form" both refer to proteins and polypeptides which are in solution and not precipitated. Usually, the soluble form is identical or very similar to the native, natural and active form of the protein. In contrast, an insoluble form is usually either a protein pellet such as inclusion bodies, or can be pelleted from solution using a standard table top centrifuge. In the case of *E. coli*, the term "expression of a protein in a soluble form" refers to expressed proteins which are in the supernatant of lysed cells after separation of soluble and insoluble substances by centrifugation, while insoluble proteins in the form of inclusion bodies or aggregates are be in the pellet of lysed cells after centrifugation.

As used herein, the term "cellular therapy" is intended to include therapies in which cellular material is injected into a patient. The cellular material is usually derived from culturing of cells in a cell culture medium, which may contain cytokines and growth factors. Examples for cellular therapies comprise human embryonic, pluripotent and induced pluripotent stem cell therapy, neural stem cell therapy, mesenchymal stem cell therapy, and hematopoietic stem cell therapy.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Embodiments

In a preferred embodiment of the present invention, an FGF-2 mutein of the present invention may be used for the cultivation of FGF-2 sensitive cells. These cells comprise but are not limited to stem cells such as pluripotent cells, embryonic stem cells, induced pluripotent stem cells, mesenchymal stem cells, bone marrow stromal cells and neural stem cells. FGF-2 is usually added at certain time points with a certain concentration to the cell culture (exact time points and concentrations depend on parameters such as the medium and cells chosen). The temperature of the cell culture is usually at about 37° C. The FGF-2 muteins of the present invention allow to reduce the frequency of FGF-2 protein added to the cell culture medium due to their higher thermostability at 37° C. and their lower susceptibility to proteases compared to wild-type protein. Preferentially, this reduction in the frequency is at least 1.5-fold, more preferentially at least 2-fold, and most preferentially at least 2.5-fold. Furthermore the FGF-2 muteins of the present invention allow to reduce the amount and/or concentration of FGF-2 added to the cell culture medium due to their higher biological activity compared to the wild-type protein. For example, instead of adding 40 ng wild-type FGF-2/mL every day to a cell culture, it may be sufficient to add 20 ng of an FGF-2 mutein/mL every day to the cell culture to reach the same cell survival or cell proliferation rate. For example, it may also be sufficient to add 40 ng of an FGF-2 mutein/mL every second day to the cell culture to reach the same cell survival or proliferation rate as compared to the addition of 40 ng wild-type FGF-2/mL every day.

Furthermore the FGF-2 muteins of the present invention allow the combination of reduction of frequency of said FGF-2 mutein addition compared to the frequency of wild-type FGF-2 addition and reduction of the amount of said FGF-2 compared to the amount of wild-type FGF-2. For example, it may be sufficient to add 20 ng of an FGF-2 mutein/mL every second day to the cell culture to reach the same cell survival or proliferation rate as compared to the addition of 40 ng wild-type FGF-2/mL every day.

In one embodiment of the present invention, FGF-2 sensitive cells may be cultured in a medium comprising an FGF-2 polypeptide of the present invention. Examples for FGF-2 sensitive cells comprise but are not limited to pluripotent cells, embryonic stem cells, induced pluripotent stem cells, mesenchymal stem cells, bone marrow stromal cells and neural stem cells.

In one embodiment of the present invention, an FGF-2 mutein of the present invention may be used for cell therapy. For this kind of therapy, cells of interest are usually cultured ex vivo. Typical applications comprise proliferation, expansion and differentiation of cells. Cytokines and growth factors such as an FGF-2 mutein of the present invention may be applied to the cells. These cultured cells may then be used for cell therapy, usually by applying the cells to a patient.

In one embodiment of the present invention, an FGF-2 mutein of the present invention may be used for therapeutic in vivo applications, for example in cardiovascular diseases, cancer, and psychiatric disorders.

In one embodiment of the present invention, an FGF-2 mutein of the present invention may be used as a reagent to stain FGF-2-binding cells. For this purpose, the FGF-2 mutein may be directly or indirectly conjugated to a fluorochrome. Direct conjugation may be achieved by methods known in the art such as chemical conjugation of fluorochromes to the FGF-2 mutein via reactive moieties such as —OH or —SH. Indirect conjugation may be achieved by methods known in the art such as biotinylation of the FGF-2 mutein and subsequent addition of an avidin- or streptavidin-fluorochrome conjugate. Examples for fluorochromes comprise but are not limited to phycoerythrin, allophycocyanin, fluorescein, peridinin chlorophyll and cyanine dyes.

In one embodiment of the present invention, an FGF-2 mutein of the present invention may be used for the immobilization of cells which specifically bind to FGF-2. Immobilization may occur at the surface and/or in the interior of a matrix. Examples for such matrices comprise but are not limited to plastics surfaces, membranes and gels. The FGF-2 immobilization may be achieved by methods known in the art such as non-covalent or covalent immobilization, for example adsorption or chemical linkage.

In one embodiment of the present invention, an FGF-2 mutein of the present invention may be used for in vivo imaging applications. FGF-2 may be labeled by a reagent that allows the tracking of FGF-2 in tissues and/or the body. Cells indirectly labeled by such a labeled FGF-2 mutein may also be tracked in tissues and/or the body. Labeling reagents comprise but are not limited to quantum dots, fluorophores, magnetic resonance imaging contrast agents, radiotracers and positron emitting isotopes.

In one embodiment of the present invention, an FGF-2 mutein of the present invention may be used for the analysis of FGF-2 binding to FGF receptors. There are at least four FGF receptors, FGFR1 to FGFR4, and due to natural alternate splicing of four fibroblast growth factor receptor genes, at least 48 different isoforms of FGFR are produced. Each receptor can be activated by several FGF proteins. In many cases, many FGF protein such as FGF-1 themselves can also activate more than one receptor. Due to their high biological affinity, the FGF-2 muteins may have a higher affinity to some FGF receptors than the wild-type FGF-2 and therefore may be superior for receptor binding studies, especially when the affinity of wild-type FGF-2 to an FGF receptor is low. The FGF-2 muteins may also be useful for selective binding to certain FGF receptors and as a consequence for induction of a selective cell signaling.

In one embodiment of the present invention, a fragment of an FGF-2 mutein of the present invention may be used. The fragment comprises the amino acid sequence which is required for FGF-2 to exert at least some of its biological activity such as binding to an FGF receptor and/or inducing effects on cells. Such a fragment also offers higher thermostability as compared to a similar fragment of the wild-type FGF-2.

The present invention also comprises nucleic acids encoding FGF-2 muteins of the present invention. In one embodiment, such a nucleic acid is used for the transformation, transfection or transduction of host cells such as bacterial cells, yeast cells, plant cells, and mammalian cells.

The present invention also comprises host cells expressing the FGF-2 of the present invention. These cells comprise but are not limited to bacterial cells, yeast cells, plant cells, and mammalian cells. In one embodiment, these host cells are used for the recombinant expression of FGF-2 muteins of the present invention. The FGF-2 polypeptide of the present invention may be obtained from the cells, for example, in a pure form by chromatographic purification of cell lysates or cell supernatants.

In one embodiment of the present invention, an FGF-2 mutein of the present invention may be formulated in buffers and solutions which preserve the biological activity. Buffering agents and solution components comprise but are not limited to Tris, Hepes, citrate, acetate, phosphate-based buffers, salts such as NaCl and KCl, surfactants such as Tween-20, Tween-80 and Triton X-100, and amino acids.

In one embodiment of the present invention, an FGF-2 mutein of the present invention may be freeze-dried to increase long-term stability of the protein. The freeze-dried formulation may contain excipients that have cryoprotective properties. Examples for such cryoprotective substances are sugars such as sucrose and trehalose, dextrins and cyclodextrins. The freeze-dried formulation may also contain excipients that serve as bulking agents. These substances form the bulk of the lyophilized product and provide an adequate structure to the cake. Examples for bulking agents are amino acids such as arginine and glycine, sugars such as lactose, mannitol and sorbitol, and polymers such as dextran and polyethylene glycol. The bulking agent may appear as crystalline or amorphous solid at the end of the lyophilization process.

In one embodiment of the present invention, an FGF-2 mutein of the present invention may be incorporated in a small, water-soluble pellet with a diameter of, for example, 1-10 mm. The pellet may contain a defined amount of an FGF-2 mutein. For cell culture, FGF-2 mutein may then be added as pellet to the culture. The pellet dissolves in the cell culture media and releases the FGF-2 mutein. Such pellets may be generated by methods known in the art such as dropping a solution containing FGF-2 into liquid nitrogen.

In another embodiment of the invention, the pellet does not dissolve directly when given into cell culture, but releases FGF-2 automatically over a certain period.

In one embodiment of the present invention, an FGF-2 mutein of the present invention is encapsulated by substances that allow a controlled release of the polypeptide. Examples for encapsulation comprises poly(lactic-co-glycolic acid) (PLGA) microspheres, alginate microspheres, hydrogels and collagen capsules, and combinations thereof.

EXAMPLES

Example 1: Sequence Description of FGF-2 Muteins

The sequences of the FGF-2 proteins of the present invention are based on the FGF-2 isoform 1 (SEQ ID NO:1, WT-isoform-1) with the following amino acid exchanges: 2x-mutein_mb (SEQ ID NO:3) having the substitutions Q56I and N102G, 3x-mutein_mb (SEQ ID NO:4) having the substitutions Q56I, N102G and K119N, 4x-mutein_mb (SEQ ID NO:5) having the substitutions Q56I, A75C, N102G and K119N, 5x-mutein_mb (SEQ ID NO:6) having the substitutions Q56I, C69S, C87S, N102G and K119N.

In the description the substitutions are given in the standard one-letter code for amino acids. The complete sequences in comparison are shown in FIG. 2.

Example 2: Cloning of DNA Vectors

Synthetic genes coding for SEQ ID NO:1, SEQ ID NO:3, SEQ ID NO:4, SEQ ID NO:5 and SEQ ID NO:6 were synthesized by an external supplier and cloned into a bacterial expression vector using standard methods. Both the genes and the expression vector were cut with the restriction enzymes BamHI and NdeI and purified by NucleoSpin® Gel and PCR Clean-Up Kit (Macherey-Nagel). For the ligation of the digested synthetic gene sequences into the digested expression vector, 50 ng gene DNA coding for either SEQ ID NO:1, SEQ ID NO:3, SEQ ID NO:4, SEQ ID NO:5 or SEQ ID NO:6 and 15.5 ng linearized vector DNA were ligated using the Quick Ligation™ Kit (NEB) in a reaction volume of 20 µL for 5 minutes at room temperature.

Example 3: Transformation of E. coli Cells for Isolation of Ligated DNA Vectors Transformation of E. coli cells with ligated DNA vectors was conducted using a standard heat shock protocol. Briefly, 0.05 mL of a competent E. coli K-12 strain (such as DH5a, XL-1 blue or JM109) and 2 µL (=6 ng DNA) of the ligation reaction of example 2 were mixed and incubated for 5 min on ice, 30 sec at 42° C. and again 2 min on ice. Then this mixture was supplemented with 250 µL SOC medium and incubated for 1 hour at 37° C. Afterwards the mixture was plated onto an LB agar plate with 50 µg kanamycin/mL as a selection marker. The agar plate was incubated overnight at 37° C. until colonies were clearly visible.

Example 4: Isolation of Expression Vector DNA

Bacterial clones were picked from the LB agar plate of example 3 and transferred into 15 mL tubes containing 3 mL LB medium with 50 µg kanamycin/mL. Those inoculated samples were incubated overnight at 37° C. and 250 rpm. The next day small-scale plasmid DNA isolations (Invisorb® Spin Plasmid Mini Two Kit, Invitek) from the incubated samples were performed. To check for correct insertions of the synthetic genes into the vector DNA, 1 µg of each isolated DNA was digested with each 1 µL BamHI and NdeI to cut out the insert. The digested DNA was analyzed by standard agarose gel electrophoresis. For a medium scale plasmid DNA isolation, positive clones were inoculated in 50 mL LB medium with 50 µg kanamycin/mL and incubated overnight at 37° C. and 250 rpm. Then plasmid DNA from the cells was isolated using the Nucleobond® PC100 Kit (Macherey-Nagel). 1 µg of isolated DNA was digested with each 1 µL of the restriction enzymes XhoI plus DraI and BamHI plus NdeI to check the presence of the insert. Digested DNA was analyzed by standard agarose gel electrophoresis. As a result, five expression vectors coding for the FGF-2 proteins WT-isoform-1 (SEQ ID NO:1), 2x-mutein_mb (SEQ ID NO:3), 3x-mutein_mb (SEQ ID NO:4), 4x-mutein_mb (SEQ ID NO:5) and 5x-mutein_mb (SEQ ID NO:6) for the expression of the proteins under control of an inducible promoter were generated. All sequences start with an ATG codon encoding for the initiator methionine. This methionine is usually proteolytically removed by E. coli during the recombinant expression.

Example 5: Transformation of E. coli with Vector DNA for Recombinant Expression of FGF-2 Proteins Transformation of E. coli cells with isolated DNA expression vectors from example 4 was conducted using a standard heat shock protocol. Briefly, 0.05 mL of an E. coli B strain such as BL21 and 1 µL containing 1-10 ng DNA of example 4 were mixed and incubated for 5 min on ice, 30 sec at 42° C. and again 2 min on ice. Then this mixture was supplemented with 0.25 mL SOC medium and incubated for 1 hour at 37° C. Afterwards the mixture was plated onto an LB agar plate with 50 µg kanamycin/mL as a selection marker. LB agar plates were incubated overnight at 37° C. until colonies were clearly visible.

Example 6: Expression of Recombinant FGF-2 Proteins in E. coli

Figure 3:
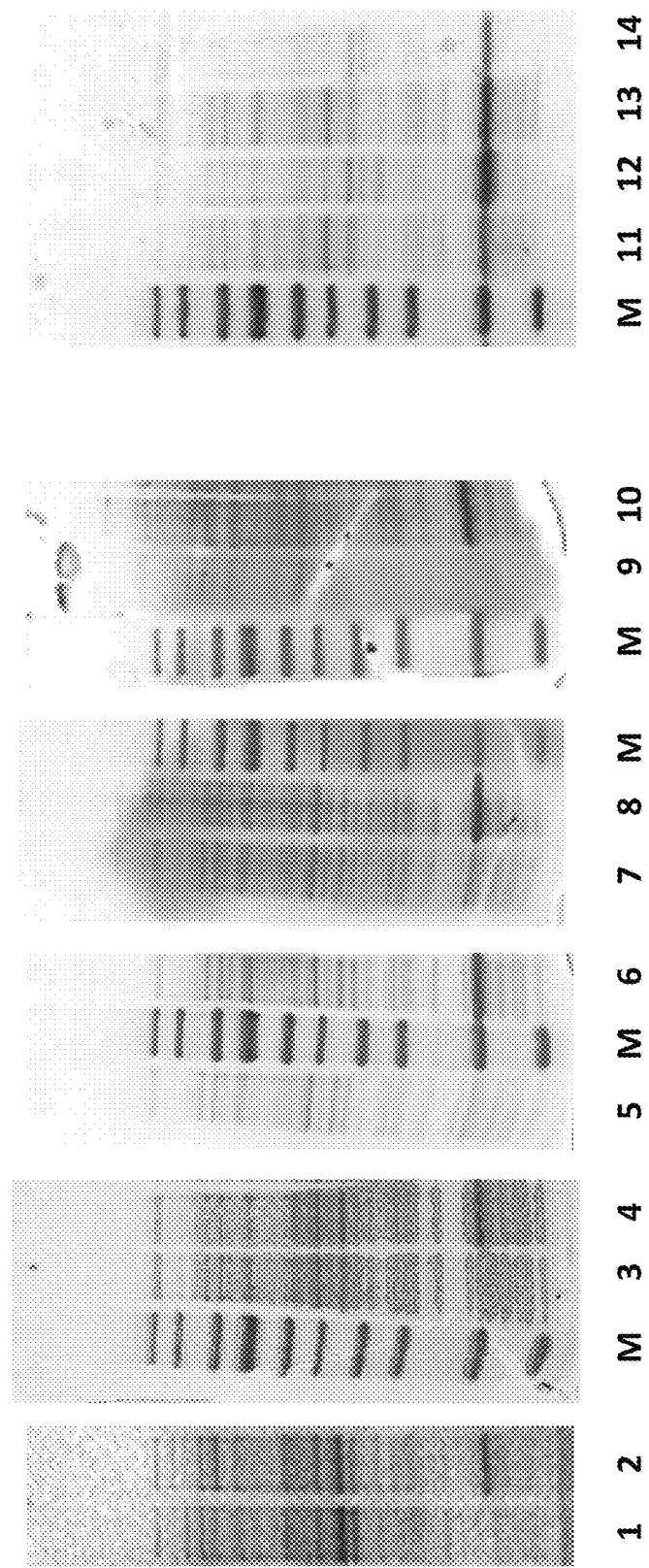
FIG. 3 shows SDS PAGE of FGF-2 polypeptides, expressed in E. coli. Coomassie-stained SDS gels of FGF-2 polypeptides expressed in E. coli. 20 µL of each cell lysate before and 5 hours after induction at 25° C. were applied to the gel. As an example, the expression of the 4x-mutein_mb is shown at induction temperatures of 37° C. and 25° C., and the cell lysates are divided into soluble (supernatant) and insoluble (pellet) fractions. The prominent band at 15 kDa corresponds to monomeric FGF-2. M: molecular weight marker with marker sizes of 170, 130, 100, 70, 55, 40, 35, 25, 15, 10 kDa (from top to bottom). WT-isoform-1: lanes 1, 2. 2x-mutein_mb: lanes 3, 4. 3x-mutein_mb: lanes 5, 6. 4x-mutein_mb: lanes 7, 8, 11, 12, 13, 14. 5x-mutein_mb: lanes 9, 10. Before induction: lanes 1, 3, 5, 7, 9. After induction: lanes, 2, 4, 6, 8, 10, 11, 12, 13, 14. Whole cell lysates: lanes 1, 2, 3, 4, 5, 6, 7, 8, 9, 10. Soluble fractions (supernatant): 11, 13. Insoluble (pellet) fractions: 12, 14. Expression at 25° C.: lanes 1, 2, 3, 4, 5, 6, 7, 8, 9, 10, 13, 14. Expression at 37° C.: 11, 12.

Bacterial clones were picked from the LB agar plates of example 5 and cell banks containing a mixture of 85% LB medium (with 50 µg kanamycin/mL and 1% glucose) and 15% glycerol were generated. For expression of each FGF-2 protein (WT-isoform-1, 2x-mutein_mb, 3x-mutein_mb, 4x-mutein_mb and 5x-mutein_mb), 50 mL LB medium (containing 50 µg kanamycin/mL and 1% glucose) was inoculated with 15-25 µL of the cell bank and incubated for 12-16 hours at 37° C. and 250 rpm overnight. The culture was then diluted with fresh LB medium containing 50 µg kanamycin/mL to an optical density at 600 nm of 0.2-0.3 in a total volume of 1 L and was further grown at 37° C. and 250 rpm until the optical density at 600 nm reached 0.6-0.8. At this point, in some cases the temperature of the culture was lowered to 25° C. 0.4 mM IPTG was added to induce the expression of FGF-2 proteins. After 5 hours of incubation at 250 rpm, cells were collected by centrifugation at 4000×g, 4° C. The supernatant was discarded, and the cells were resuspended in 5 mL of 20 mM $NaH_2PO_4$, 1 mM $MgCl_2$, pH 8.0, per gram of cell pellet. Samples of resuspended cells were used for SDS PAGE of uninduced and induced cells after 5 hours (FIG. 3, lanes 1-10) with SDS PAGE conditions as described below. To extract the FGF-2 proteins, the resuspended cells were lysed using a high pressure homogenisator with a pressure of 1250 bar. Benzonase® nuclease (Merck Millipore) was added to reduce the viscosity of the solution. The insoluble material was pelleted by centrifugation at 7000×g, 4° C. for 2 hours, and the supernatant containing soluble FGF-2 proteins was further used for purification. 20 µL of each sample (insoluble pellet and soluble supernatant) were mixed with SDS sample buffer (final concentration of 50 mM Tris/HCl pH 6.8, 2% SDS, 10% glycerol, 0.01% bromophenol blue, 3.5% 2-mercaptoethanol), heated for 5 minutes at 95° C. and analyzed by SDS PAGE stained with Coomassie (FIG. 3, lanes 11-14). All FGF-2 proteins were comparably expressed at high-level mainly in a soluble form when expressed at 25° C. for 5 hours. Expression at 37° C. further increased the level of FGF-2 protein, but most of the protein became insoluble. As an example, this is shown for the 4×-mutein_mb in lanes 11-14; the same effect was seen for the other FGF-2 proteins.

Figure 4:
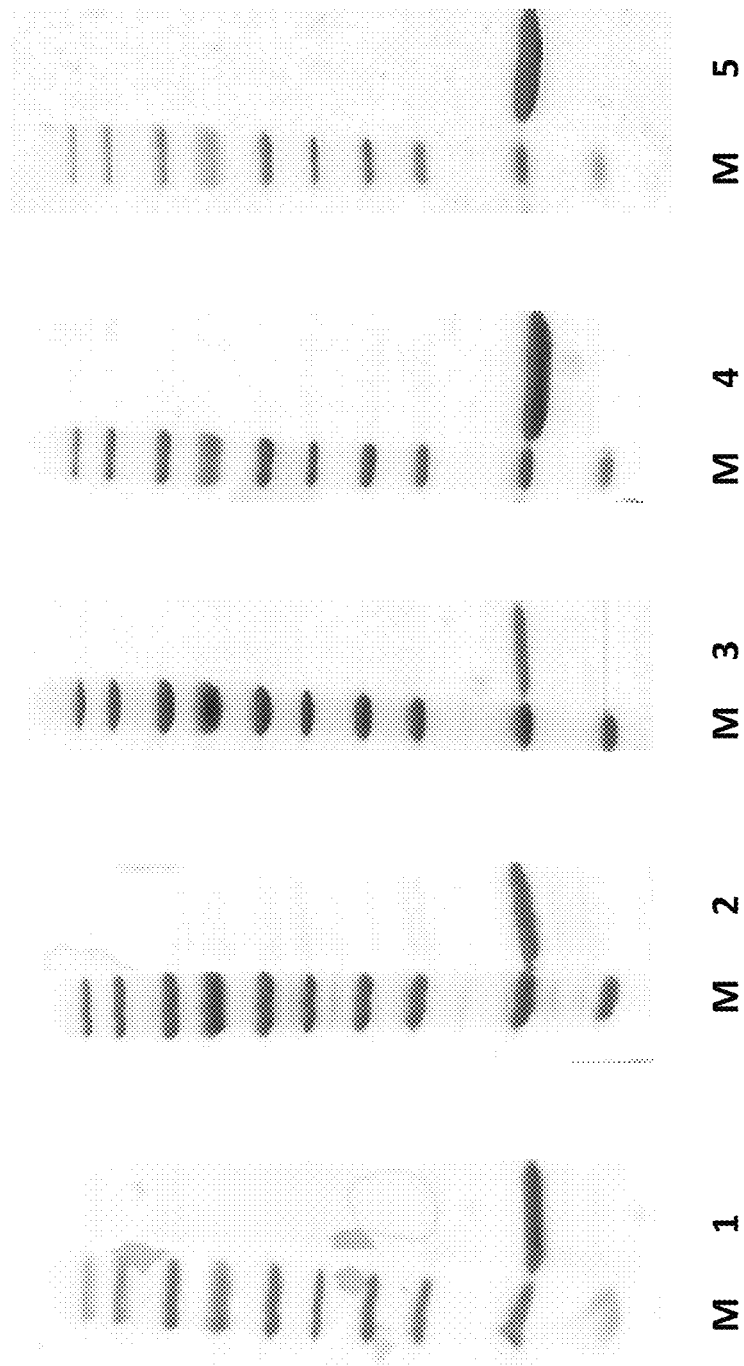
FIG. 4 shows SDS PAGE of purified FGF-2 polypeptides. Coomassie-stained SDS gel of FGF-2 polypeptides, purified by Heparin sepharose chromatography. 20 µL, of each protein was applied to the gel. M: molecular weight marker with marker sizes of 170, 130, 100, 70, 55, 40, 35, 25, 15, 10 kDa (from top to bottom). WT-isoform-1: lane 1. 2x-mutein_mb: lane 2. 3x-mutein_mb: lane 3. 4x-mutein_mb: lane 4. 5x-mutein_mb: lane 5.

Example 7: Purification of Recombinant FGF-2 Proteins 2 mL of each supernatant of lysed cells containing FGF-2 proteins of example 6 (WT-isoform-1, 2×-mutein_mb, 3×-mutein_mb, 4×-mutein_mb and 5×-mutein_mb) was diluted 1:2 with 25 mM $NaH_2PO_4$, 50 mM NaCl, pH 7.4, and processed by Heparin sepharose chromatography. Therefore, a 1 mL HiTrap™ Heparin HP column (GE Healthcare) was equilibrated with 25 mM $NaH_2PO_4$, 50 mM NaCl, pH 7.4. The FGF-2 protein containing supernatants were individually applied to the column. To remove background proteins, 5 column volumes of 25 mM $NaH_2PO_4$, 1 M NaCl, pH 7.4, as a wash buffer were applied to the column. FGF-2 proteins were eluted with 25 mM $NaH_2PO_4$, 1.5 M NaCl, pH 7.4. 20 µL, of each eluate containing purified FGF-2 protein was mixed with SDS sample buffer (final concentration of 50 mM Tris/HCl pH 6.8, 2% SDS, 10% glycerol, 0.01% bromophenol blue, 3.5% 2-mercaptoethanol), heated for 5 minutes at 95° C. and analyzed by SDS PAGE stained with Coomassie (FIG. 4). All FGF-2 proteins (WT-isoform-1, 2×-mutein_mb, 3×-mutein_mb, 4×-mutein_mb and 5×-mutein_mb) showed a similar purity of 90-95% based on SDS gel analysis.

Example 8: Determination of Biological Activity

Figure 5:
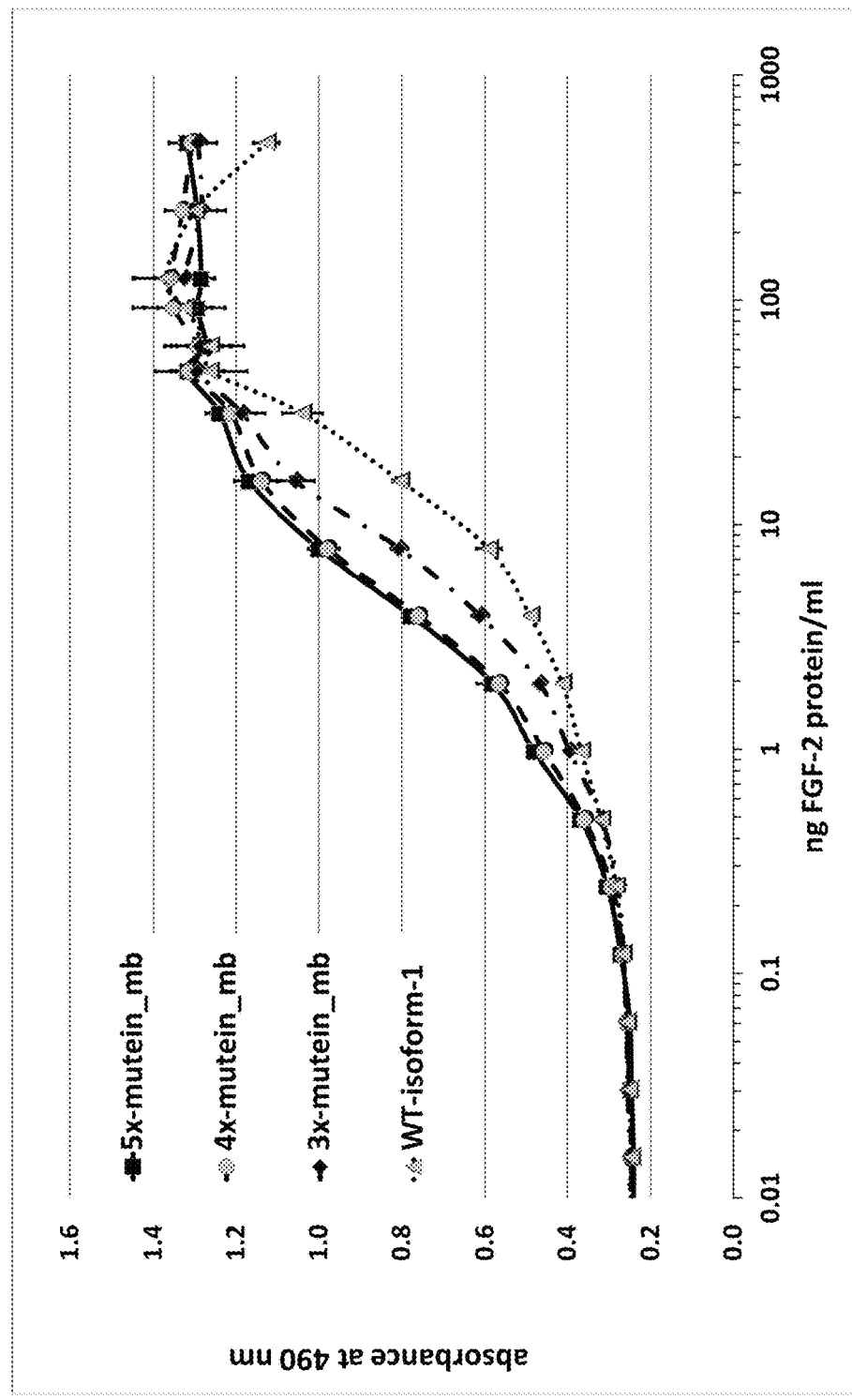
FIG. 5 shows Dose-response curve of FGF-2 dependent proliferation of 3T3 A31 cells. Different amounts of purified wild-type FGF-2 protein ("WT-isoform-1", grey triangles) and purified muteins of the present invention ("3x-mutein_mb", black diamonds; "4x-mutein_mb", grey circles; and "5x-mutein_mb", black squares) were added to the cells, and the proliferation was measured at 490 nm using a colorimetric assay by the conversion of -(4,5-dimethylthiazol-2-yl)-5-(3-carboxymethoxyphenyl)-2-(4-sulfophenyl)-2H-tetrazolium (MTS) to formazan by viable cells. The measurements were performed in quadruplicate.

Purified FGF-2 proteins of example 7 proteins (WT-isoform-1, 3×-mutein_mb, 4×-mutein_mb and 5×-mutein_mb) were analyzed in a proliferation assay using 3T3 A31 fibroblast cells on the basis of Robinson C. J. and Gaines-Das R., Growth Factors 11: 9-16 (1994). The cells were grown in serum-free DMEM/F12 medium, supplemented with albumin, insulin, transferrin, selenium, fibronectin and dexamethasone, at 37° C. and incubated with different concentrations of FGF-2 proteins. The protein content of FGF-2 proteins was determined by Bradford assay. After 2 days, the number of viable cells was determined by the addition of 20 µL, 3-(4,5-dimethylthiazol-2-yl)-5-(3-carboxymethoxyphenyl)-2-(4-sulfophenyl)-2H-tetrazolium (MTS) per well to the samples. The cells were incubated for 180 minutes at 37° C. and the resulting formazan product was detected by absorbance measurement at 490 nm. The measurements were performed in quadruplicate. The half-maximal activity or effective dose, ED50 [ng/mL], was determined from the dose-response-curves (FIG. 5, table 1). Smaller ED50 values represent higher activities of the FGF-2 proteins. The ED50 is generally referred to as 1 unit, and the specific activity [units/mg] can be calculated by the formula: specific activity [units/mg] =1E+06/ED50 [ng/mL]. For the determination of the calibrated specific activity [international units per mg protein, IU/mg], the bioassay was calibrated using the 1st International Standard 90/712 (National Institute for Biological Standards and Control, Potters Bar, Hertfordshire, EN6 3QG), and the specific activities [U/mg] were corrected by a factor determined by the calibration to obtain calibrated specific activities [IU/mg]. By calibration of the assay, the values of biological activity are not assay-dependent, allowing for a direct comparison of biological activities.

The analyzed FGF-2 proteins 3×-mutein_mb, 4×-mutein_mb and 5×-mutein_mb all showed a higher biological activity than the wild-type FGF-2 (table 1). The first unexpected result was an increased activity of the 3×-mutein_mb compared to the wild-type FGF-2, which was about 1.9-fold higher. Surprisingly, the exchange of both surface-exposed cysteines to serine in the 3×-mutein_mb to generate the 5×-mutein_mb further increased the biological activity about 1.8-fold, resulting in the highest biological activity of the analyzed FGF-2 proteins. This was unexpected because the substitution of only the surface-exposed cysteines in the wild-type without further substitutions did not result in any activity differences to the wild-type, as published many times in the literature and described in the Background of the invention above. Furthermore, the combination of exchange of one surface cysteine C96S in combination with the substitutions Q65I+ N111G mutations in FGF-2 isoform 3 as described in US20120225479 increased the expression level of the protein in human cells compared to the wild-type protein, but no increase of biological activity was observed.

Surprisingly, the exchange of alanine-75 to cysteine in the 3×-mutein_mb to generate the 4×-mutein_mb also increased the biological activity about 1.6-fold.

TABLE 1

ED50 values and calibrated specific activity of recombinant purified FGF-2 proteins based on a proliferation assay using 3T3 A31 cells, measured in quadruplicate. Lower ED50 values reflect higher biological activities. The calibrated specific activity of WT-isoform-1 was set to 100%. IU, international units.

| FGF-2 protein | ED50 (ng/mL) | Calibrated specific activity (IU/mg) | Relative activity |
|---|---|---|---|
| WT-isoform-1 (SEQ ID NO:1) | 12.8 ± 0.5 | 0.9E+06 | 100% |
| 3×-mutein_mb (SEQ ID NO:4) | 6.8 ± 0.3 | 1.7E+06 | 189% |
| 4×-mutein_mb (SEQ ID NO:5) | 4.3 ± 0.2 | 2.7E+06 | 300% |
| 5×-mutein_mb (SEQ ID NO:6) | 3.7 ± 0.2 | 3.2E+06 | 356% |

Example 9: Analysis of Thermostability of Recombinant FGF-2 Proteins

The purified FGF-2 protein 5×-mutein_mb of example 7 was analyzed regarding its thermostability at 37° C. in comparison to wild-type FGF-2 ("WT-isoform-1") of example 7.

Figure 6:
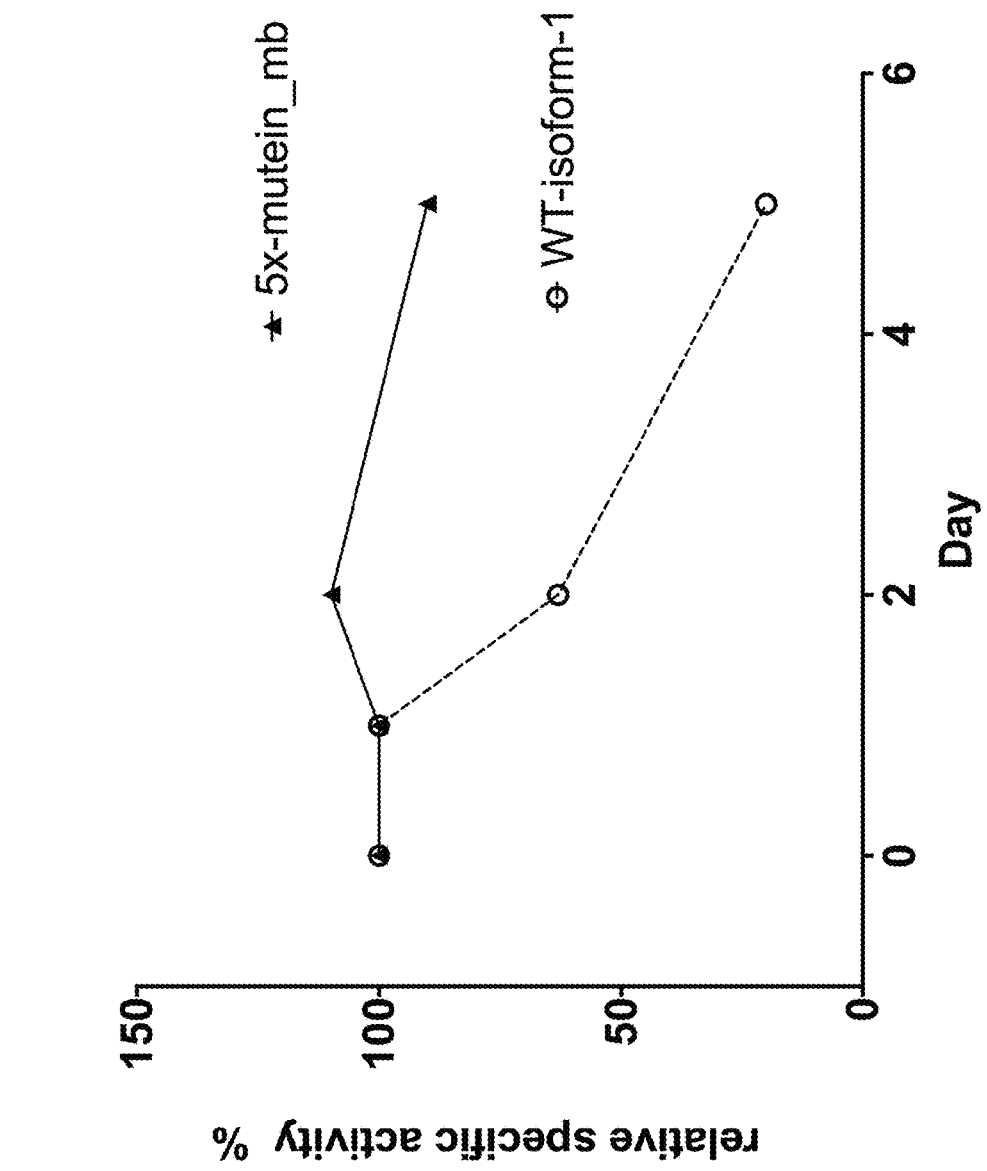
FIG. 6 shows thermostability of wild-type FGF-2 protein ("WT-isoform-1", open circles) and 5x-mutein_mb (closed triangles) at 37° C., measured as remaining specific activity after incubation at 37° C. Both proteins were subjected to incubation at 37° C. in a buffered solution for 5 days. Samples were taken before the incubation and on days 1, 2 and 5. The calibrated specific activity of each sample was determined as described in example 8. The calibrated specific activity of each protein before the incubation ("day 0") was set to 100% ("relative specific activity").

Both proteins were incubated at a concentration of 0.1 mg protein/ml in 25 mM NaH$_2$PO$_4$, 50 mM NaCl, pH 7.4 at 37° C. over a period of 5 days. Samples were taken before incubation ("day 0") and after 1, 2 and 5 days. Calibrated specific activities of these samples were determined as described in example 8. The calibrated specific activity of each protein at day 0 was set to 100%. The calibrated specific activity of wild-type FGF-2 decreased to 60% (day 2) and to 20% (day 5) of the initial calibrated specific activity, demonstrating the low thermostability of the wild-type FGF-2 protein (FIG. 6). The calibrated specific activity of FGF-2 protein 5x-mutein_mb remained unchanged until day 2 and decreased to 90% of the initial calibrated specific activity at day 5, demonstrating the high thermostability of an FGF-2 5x-mutein.

The purified FGF-2 proteins WT-isoform-1, 3x-mutein_mb, 4x-mutein_mb and 5x-mutein_mb of example 7 were also analyzed by SDS PAGE under reducing and non-reducing conditions after thermal stressing. Therefore, the proteins were incubated at a concentration of 0.1 mg protein/ml in 25 mM NaH$_2$PO$_4$, 50 mM NaCl, pH 7.4 at 37° C. for 3 days. Samples were taken before incubation ("day 0") and after 3 days. Equal amounts of each FGF-2 protein was mixed with SDS sample buffer (final concentration of 50 mM Tris/HCl pH 6.8, 2% SDS, 10% glycerol, 0.01% bromophenol blue, 3.5% 2-mercaptoethanol in the case of reducing conditions), heated for 5 minutes at 95° C. and analyzed by SDS PAGE stained with Coomassie (FIG. 7). Under both reducing and non-reducing conditions, the amount of wild-type FGF-2 (WT-isoform-1) as determined by SDS PAGE has decreased by 40% after 3 days of incubation at 37° C., compared to the initial protein amount (FIG. 8). Surprisingly, the amount of 3x-mutein_mb has decreased by only 20% after 3 days of incubation at 37° C., compared to the initial protein amount. More surprisingly, the amount of 4x-mutein_mb and 5x-mutein_mb remained unchanged after 3 days of incubation at 37° C., compared to the initial protein amount. This result reflects the increased thermostability of an FGF-2 3x-mutein, an FGF-2 4x-mutein and an FGF-2 5x-mutein.

Therefore a specific combination of mutations as present in the 3x-mutein_mb, the 4x-mutein_mb and the 5x-mutein_mb, respectively, is required to generate an FGF-2 polypeptide with higher thermostability and higher biological activity than wild-type FGF-2 polypeptide.

Example 10: Analysis of Stability of Recombinant FGF-2 Proteins to Proteolytic Degradation Purified FGF-2 proteins of example 7 (WT-isoform-1, 3x-mutein_mb, 4x-mutein_mb and 5x-mutein_mb) were incubated in 25 mM NaH$_2$PO$_4$, 50 mM NaCl, 2 mM CaCl$_2$, pH 7.4, containing porcine trypsin (Sigma) at a molar ratio of 1:8 (trypsin:FGF-2 protein), respectively, for 80 minutes at 37° C. The initial concentration of FGF-2 proteins was 0.2 mg/mL. Before the addition of trypsin ("0 minutes") and after incubation of 30 and 80 minutes, 20 µL of the incubated solution was mixed with SDS sample buffer (final concentration of 50 mM Tris/HCl pH 6.8, 2% SDS, 10% glycerol, 0.01% bromophenol blue, 3.5% 2-mercaptoethanol, heated for 5 minutes at 95° C. and analyzed by SDS PAGE (FIG. 9). After 30 minutes of incubation with trypsin, 85% of the 15 kDa band of WT-isoform-1 disappeared (FIG. 10), and several shorter (degraded) forms <15 kDa are visible. In contrast, for 3x-mutein_mb, 4x-mutein_mb and 5x-mutein_mb only 63-67% of the 15 kDa band disappeared. Furthermore, degradation products <15 kDa are less visible for 3x-mutein_mb, 4x-mutein_mb and 5x-mutein_mb than for WT-isoform-1. After 80 minutes of incubation with trypsin, 97% of the 15 kDa band of WT-isoform-1 disappeared. In contrast, for 3x-mutein_mb, 4x-mutein_mb and 5x-mutein_mb only 90-93% of the 15 kDa band disappeared. Based on the kinetics of the proteolytic degradation (FIG. 10), it can be estimated that the initial (linear) reaction velocity of proteolytic degradation of WT-isoform-1 is about 1.5-fold faster than for the FGF-2 muteins.

This result reflects the increased stability to proteases of an FGF-2 3x-mutein, an FGF-2 4x-mutein and an FGF-2 5x-mutein.

Therefore a specific combination of mutations as present in the 3x-mutein_mb, the 4x-mutein_mb and the 5x-mutein_mb, respectively, is required to generate a FGF-2 polypeptide with higher thermostability, higher biological activity and higher stability to proteases than wild-type FGF-2 polypeptide.

Example 11: Mass Spectrometric Analysis of 5x-Mutein_mb

Purified 5x-mutein_mb of example 7 was analyzed by electrospray ionization mass spectrometry (ESI-MS) under reducing conditions. The calculated mass of the 5x-mutein_mb (SEQ ID NO:6) is 16289.6. Two mass signals of 16288.8 and 16192.3 were detected (FIG. 11). The value of 16288.8 corresponds to the full-length form of SEQ ID NO:6, while 16192.3 is compatible with a fragment of the 5x-mutein_mb which is missing the N-terminal proline residue (calculated mass: 16192.5).

SEQUENCES

```
                                          SEQ ID NO: 1
human wild-type isoform-1 FGF-2 (protein)
Uniprot entry P09038, http://www.uniprot.org
PALPEDGGSG AFPPGHFKDP KRLYCKNGGF FLRIHPDGRV

DGVREKSDPH IKLQLQAEER GVVSIKGVCA NRYLAMKEDG

RLLASKCVTD ECFFFERLES NNYNTYRSRK YTSWYVALKR

TGQYKLGSKT GPGQKAILFL PMSAKS

SEQ ID NO: 2
human wild-type isoform-3 FGF-2 (protein)
Uniprot entry P09038, http://www.uniprot.org
MAAGSITTLP ALPEDGGSGA FPPGHFKDPK RLYCKNGGFF

LRIHPDGRVD GVREKSDPHI KLQLQAEERG VVSIKGVCAN

RYLAMKEDGR LLASKCVTDE CFFFERLESN NYNTYRSRKY

TSWYVALKRT GQYKLGSKTG PGQKAILFLP MSAKS

SEQ ID NO: 3
2x-mutein_mb (protein)
PALPEDGGSG AFPPGHFKDP KRLYCKNGGF FLRIHPDGRV

DGVREKSDPH IKLQLIAEER GVVSIKGVCA NRYLAMKEDG

RLLASKCVTD ECFFFERLES NGYNTYRSRK YTSWYVALKR

TGQYKLGSKT GPGQKAILFL PMSAKS
```

SEQ ID NO: 5
4x-mutein_mb (protein)
PALPEDGGSG AFPPGHFKDP KRLYCKNGGF FLRIHPDGRV

DGVREKSDPH IKLQLIAEER GVVSIKGVCA NRYLCMKEDG

RLLASKCVTD ECFFFERLES NGYNTYRSRK YTSWYVALNR

TGQYKLGSKT GPGQKAILFL PMSAKS

The amino acids in bold and underlined letters discriminate the SEQ ID NO:3 from SEQ ID NO:1.

SEQ ID NO: 4
3x-mutein_mb (protein)
PALPEDGGSG AFPPGHFKDP KRLYCKNGGF FLRIHPDGRV

DGVREKSDPH IKLQLIAEER GVVSIKGVCA NRYLAMKEDG

RLLASKCVTD ECFFFERLES NGYNTYRSRK YTSWYVALNR

TGQYKLGSKT GPGQKAILFL PMSAKS

The amino acids in bold and underlined letters discriminate the SEQ ID NO:4 from SEQ ID NO:1.
The amino acids in bold and underlined letters discriminate the SEQ ID NO:5 from SEQ ID NO:1.

SEQ ID NO: 6
5x-mutein_mb (protein)
PALPEDGGSG AFPPGHFKDP KRLYCKNGGF FLRIHPDGRV

DGVREKSDPH IKLQLIAEER GVVSIKGVSA NRYLAMKEDG

RLLASKSVTD ECFFFERLES NGYNTYRSRK YTSWYVALNR

TGQYKLGSKT GPGQKAILFL PMSAKS

The amino acids in bold and underlined letters discriminate the SEQ ID NO:6 from SEQ ID NO:1.

---

What is claimed is:

1. A fibroblast growth factor-two (FGF-2) polypeptide that differs from the wild-type FGF-2 (SEQ ID NO:1) at least at amino acid positions 56, 102 and 119, wherein the differences are Q56I, N102G and K119N substitutions, and wherein said FGF-2 polypeptide has a higher thermostability, higher biological activity and higher resistance to proteolytic degradation than wild-type FGF-2.

2. An FGF-2 polypeptide according to claim 1, wherein said FGF-2 polypeptide has the sequence of SEQ ID NO:4.

3. An FGF-2 polypeptide according to claim 1, wherein said FGF-2 polypeptide additionally differs from the wild-type FGF-2 at positions 69 and 87, wherein the additional differences are C69S and C87S substitutions.

4. An FGF-2 polypeptide according to claim 3, wherein said FGF-2 polypeptide has the sequence of SEQ ID NO:6.

5. A method for culturing FGF-2 sensitive cells in a medium, the method comprising the step of cultivation of FGF-2 sensitive cells, wherein said medium comprises an FGF-2 polypeptide according to claim 1.

6. A method according to claim 5, wherein said sensitive cells are selected from the group consisting of pluripotent cells, embryonic stem cells, induced pluripotent stem cells, mesenchymal stem cells, bone marrow stromal cells and neural stem cells.

* * * * *